(12) United States Patent
Lynch et al.

(10) Patent No.: US 8,573,212 B2
(45) Date of Patent: Nov. 5, 2013

(54) REINFORCING MEMBER FOR A PATIENT INTERFACE

(75) Inventors: Susan Robyn Lynch, Epping (AU); Robin Garth Hitchcock, Carlingford (AU); Aaron Samuel Davidson, Newport (AU); Lee James Veliss, West Ryde (AU); David John Worboys, Belrose (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 13/592,801

(22) Filed: Aug. 23, 2012

(65) Prior Publication Data

US 2012/0312304 A1 Dec. 13, 2012

Related U.S. Application Data

(63) Continuation of application No. 11/794,957, filed as application No. PCT/AU2006/000033 on Jan. 12, 2006, now Pat. No. 8,261,746.

(60) Provisional application No. 60/643,121, filed on Jan. 12, 2005.

(51) Int. Cl.
*A62B 18/02* (2006.01)

(52) U.S. Cl.
USPC .............. 128/206.24; 128/205.25; 128/206.28

(58) Field of Classification Search
USPC .............. 128/205.25, 206.21, 206.24, 206.28
See application file for complete search history.

(56) References Cited

U.S. PATENT DOCUMENTS

| 5,074,297 | A | 12/1991 | Venegas |
| 6,112,746 | A | 9/2000 | Kwok et al. |
| 6,467,483 | B1 | 10/2002 | Kopacko et al. |
| 6,729,333 | B2 | 5/2004 | Barnett et al. |
| 6,772,760 | B2 | 8/2004 | Frater et al. |
| 6,823,869 | B2 | 11/2004 | Raje et al. |
| 7,069,933 | B2 | 7/2006 | Kwok et al. |
| 7,523,754 | B2 | 4/2009 | Lithgow et al. |
| 8,261,746 | B2 * | 9/2012 | Lynch et al. ............. 128/206.24 |

(Continued)

FOREIGN PATENT DOCUMENTS

| WO | WO 03/105921 | 12/2003 |
| WO | WO 2004/022146 | 3/2004 |
| WO | WO 2005/053781 | 6/2005 |

OTHER PUBLICATIONS

Second Office Action issued in a corresponding Chinese Application No. 200910209683.0 (Nov. 12, 2012) with English translation thereof.

(Continued)

*Primary Examiner* — Lynne Anderson
(74) *Attorney, Agent, or Firm* — Nixon & Vanderhye P.C.

(57) ABSTRACT

A patient interface includes a frame, a cushion, and a reinforcing member. The cushion has a non-face-contacting portion connected to the frame and a face-contacting portion adapted to engage the patient's face in use. The face-contacting portion includes a side wall and a flexible membrane extending from the side wall. The reinforcing member is provided to at least a portion of an interior and/or exterior surface of the side wall of the cushion. The reinforcing member provides reinforcement to the side wall of the cushion to at least limit lateral expansion of the cushion in use. The reinforcing member may have a stiffness that is selectively varied along its length.

20 Claims, 41 Drawing Sheets

(56) References Cited

U.S. PATENT DOCUMENTS

| | | | |
|---|---|---|---|
| 2001/0020474 | A1 | 9/2001 | Hecker et al. |
| 2002/0043265 | A1 | 4/2002 | Barnett et al. |
| 2003/0075180 | A1 | 4/2003 | Raje et al. |
| 2003/0196656 | A1 | 10/2003 | Moore et al. |
| 2003/0217746 | A1 | 11/2003 | Gradon et al. |
| 2004/0118406 | A1 | 6/2004 | Lithgow et al. |
| 2004/0144386 | A1 | 7/2004 | Frater et al. |
| 2006/0042629 | A1 | 3/2006 | Geist |
| 2009/0000623 | A1 | 1/2009 | Lynch et al. |

OTHER PUBLICATIONS

International Search Report for PCT/AU2006/000033 mailed Feb. 16, 2006.
Written Opinion for PCT/AU2006/000033 mailed Feb. 16, 2006 (6 pages).
International Preliminary Report on Patentability, PCT/AU2006/000033 (Jul. 17, 2007).
Extended Search Report issued in European Appln. No. 06704769.6 (Sep. 10, 2009).
Examination Report issued in related Australian Appln. 2006206041 (Aug. 30, 2010).
Office Action issued in related Japanese Appin. 2007-550637 (Apr. 26, 2011) with English translation.
Office Action issued in related European appln. 06704769.6 (Sep. 14, 2011).
Chinese Office Action issued in related Chinese Appln. 200910209683.0 (Feb. 17, 2012) with English translation.
Japanese Office Action issued in related Japanese Appln. 2007-550637 (Apr. 17, 2012) with English translation.

\* cited by examiner

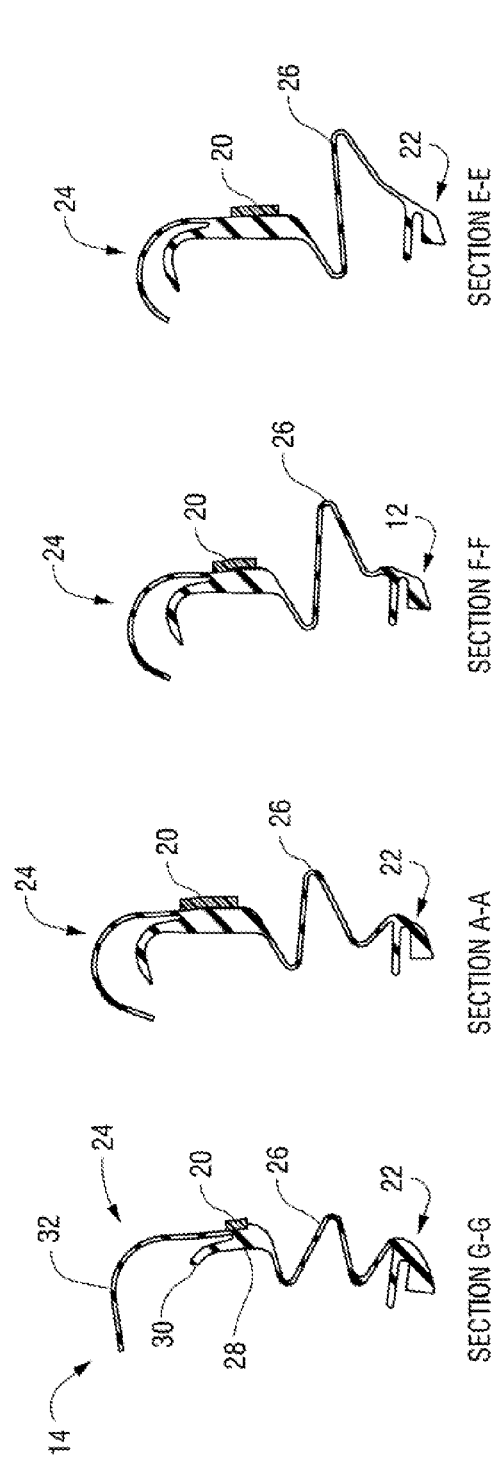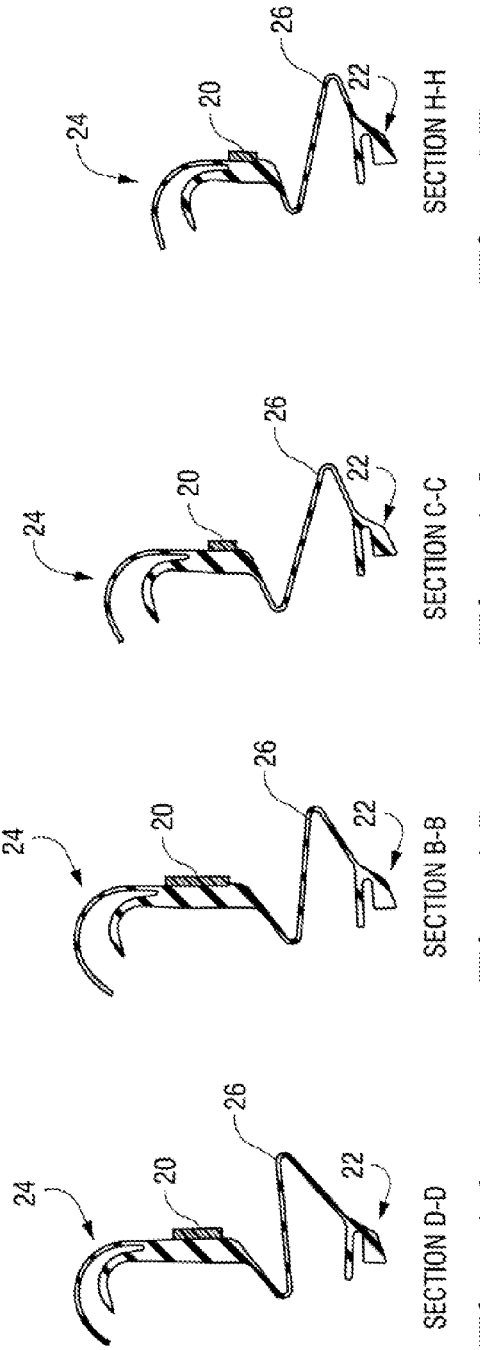

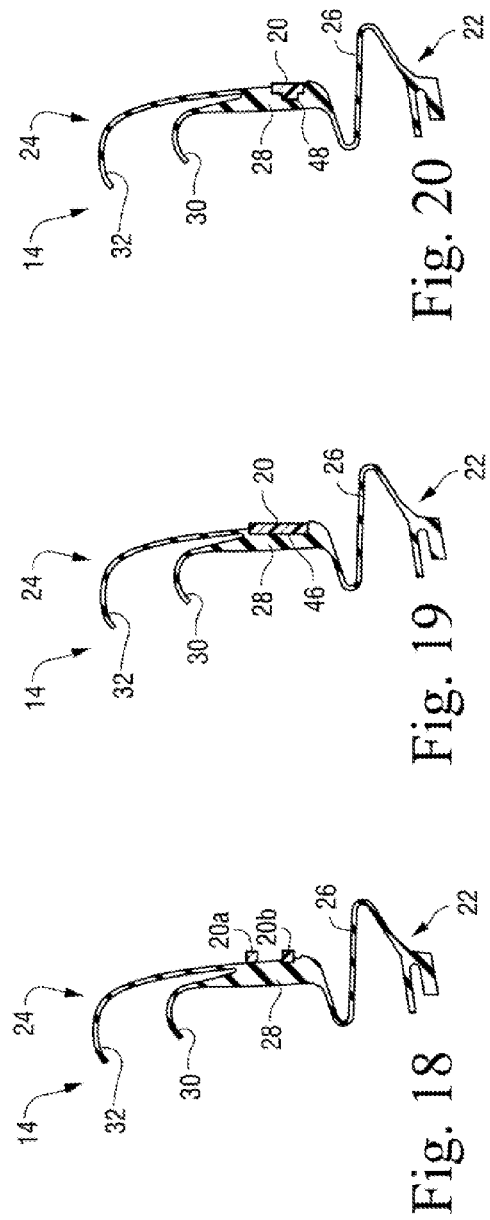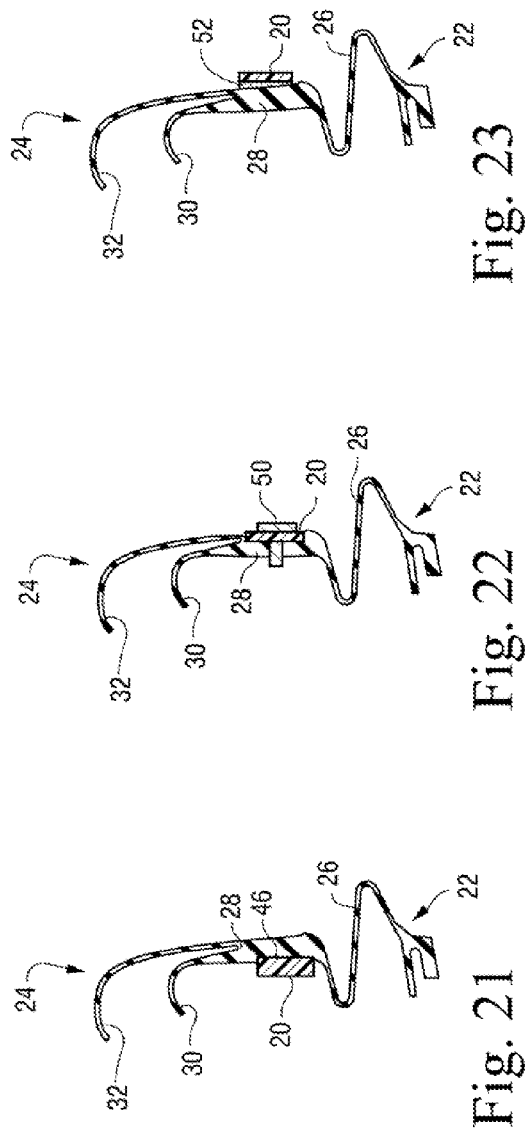

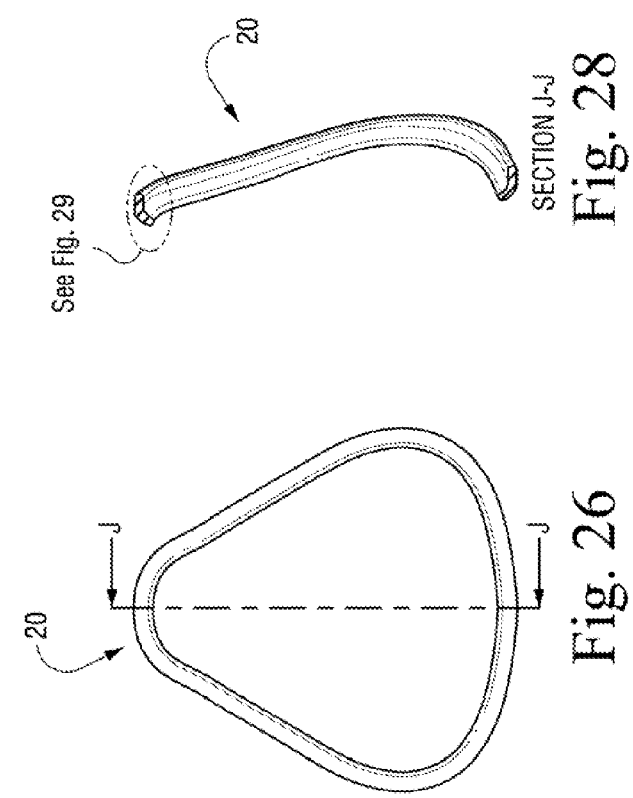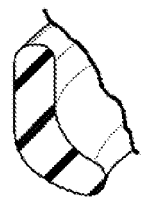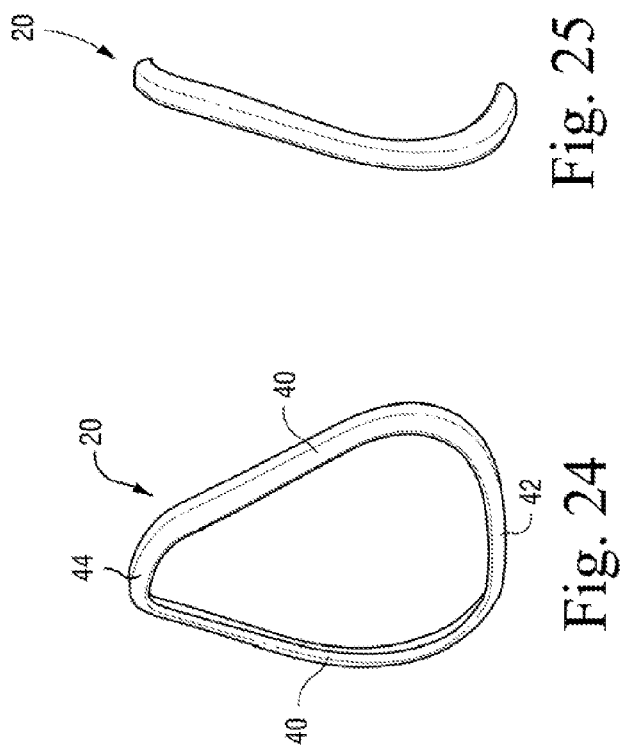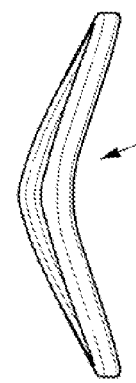

REINFORCING MEMBER FOR A PATIENT INTERFACE

CROSS-REFERENCE TO RELATED APPLICATIONS

This application is a continuation of U.S. patent application Ser. No. 11/794,957, filed Jun. 19, 2008, allowed, which is the U.S. national phase of international application No. PCT/AU2006/000033, filed Jan. 12, 2006, which designated the U.S. and claims the benefit of U.S. Provisional Application No. 60/643,121, filed Jan. 12, 2005, the entirety of each of which is incorporated herein by reference.

FIELD OF THE INVENTION

The present invention relates to a reinforcing member for a patient interface, the patient interface being used in the treatment, e.g., of Sleep Disordered Breathing (SDB) with Non-Invasive Positive Pressure Ventilation (NIPPY).

BACKGROUND OF THE INVENTION

Patient interfaces typically include a rigid shell or frame and a soft face-contacting cushion. The cushion spaces the frame away from the patient's face. The frame and cushion define a cavity which receives the patient's nose or nose and mouth. The frame and cushion are held in position on the patient's face by a headgear assembly.

A known patient interface, commercially sold under the name of Activa® by ResMed Ltd., includes a cushion having a gusset portion. Further details and embodiments of this cushion are disclosed in U.S. patent application Ser. No. 10/655,622, filed Sep. 5, 2003, the entirety of which is hereby incorporated herein by reference.

The gusset portion is positioned between the frame-contacting side and the face-contacting side of the cushion. In one embodiment described in the application, a reinforcing ring is provided between the gusset portion and the face-contacting side. The reinforcing ring acts as a stiffening hoop reducing the tendency of the cushion to expand at that point when under pressure. In one form, the reinforcing ring is made from polycarbonate and is overmolded or push-fit.

A need in the art has developed to provide improvements to the above-described reinforcing ring to limit expansion of the cushion when under pressure.

SUMMARY OF THE INVENTION

One aspect of the invention is to provide a patient interface having a reinforcing member that at least limits lateral expansion of the cushion in use.

Another aspect of the invention is to provide a patient interface having a reinforcing member that varies a level of reinforcement being provided to selected regions of the cushion.

Another aspect of the invention relates to a patient interface that includes a frame, a cushion, and a reinforcing member. The cushion has a non-face-contacting portion connected to the frame and a face-contacting portion adapted to engage the patient's face in use. The face-contacting portion includes a side wall and a flexible membrane extending from the side wall. The reinforcing member is provided to at least a portion of an interior and/or exterior surface of the side wall of the cushion. The reinforcing member provides reinforcement to the side wall of the cushion to at least limit lateral expansion of the cushion in use. The reinforcing member has a stiffness that is selectively varied along its length.

Yet another aspect of the invention relates to a patient interface including a frame, a cushion, and a reinforcing member. The cushion has a non-face-contacting portion connected to the frame and a face-contacting portion adapted to engage the patient's face in use. The face-contacting portion includes a side wall and a flexible membrane extending from the side wall. The reinforcing member is provided to at least a portion of an interior and/or exterior surface of the side wall of the cushion. The reinforcing member provides reinforcement to the side wall of the cushion to at least limit lateral expansion of the cushion in use. The reinforcing member includes at least one reinforcing rib integrally molded with the side wall of the cushion.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 9-17 are cross-sectional views through a cushion having a reinforcing member constructed according to another embodiment of the present invention;

FIGS. 18-23 are cross-sectional views illustrating the attaching of a reinforcing member to a cushion according to alternative embodiments of the present invention;

FIGS. 24-29 are isolated views of a reinforcing member removed from a cushion according to another embodiment of the present invention;

DETAILED DESCRIPTION OF ILLUSTRATED EMBODIMENTS

Figure 1:
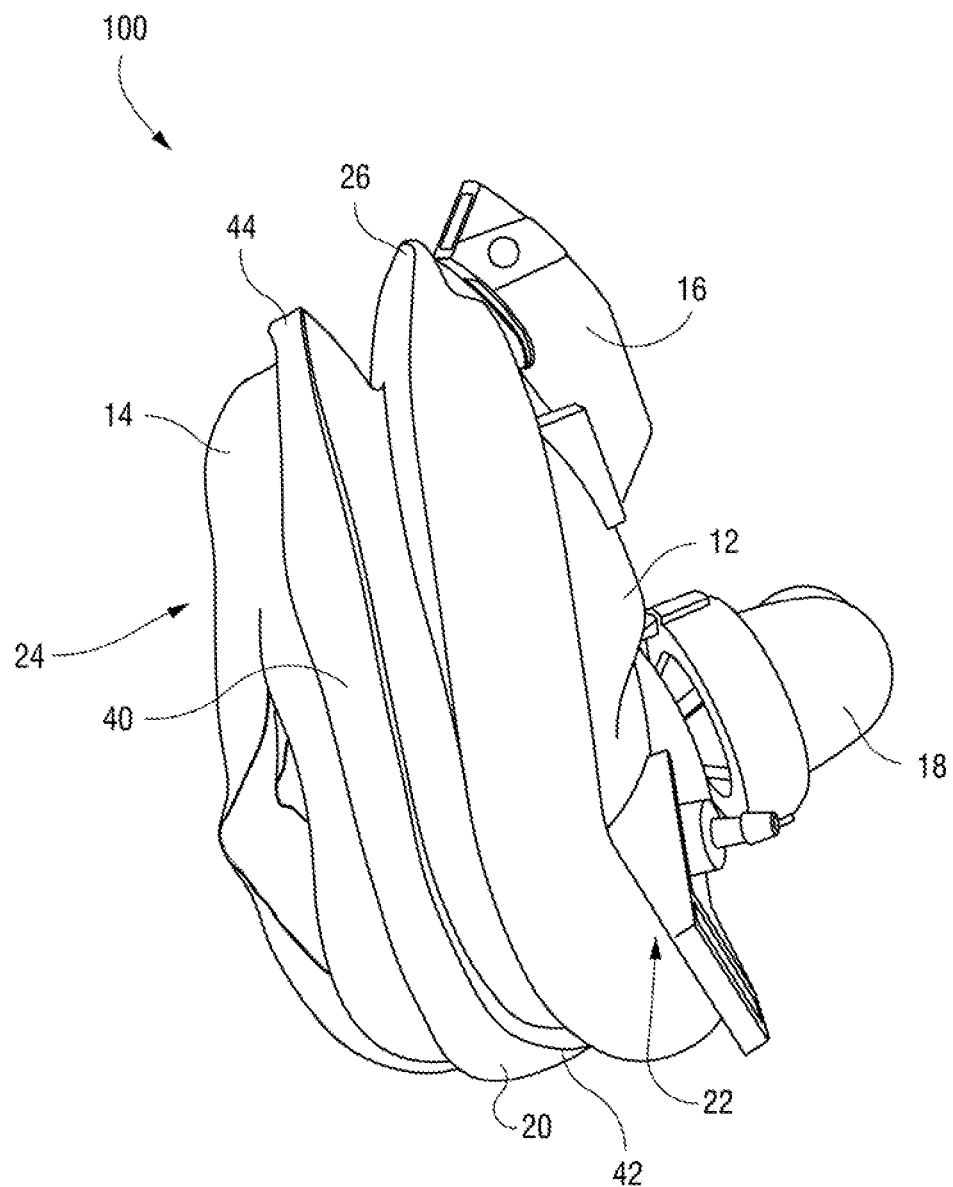
FIGS. 1-2 illustrate a patient interface including a reinforcing member constructed according to an embodiment of the present invention.
Figure 2:
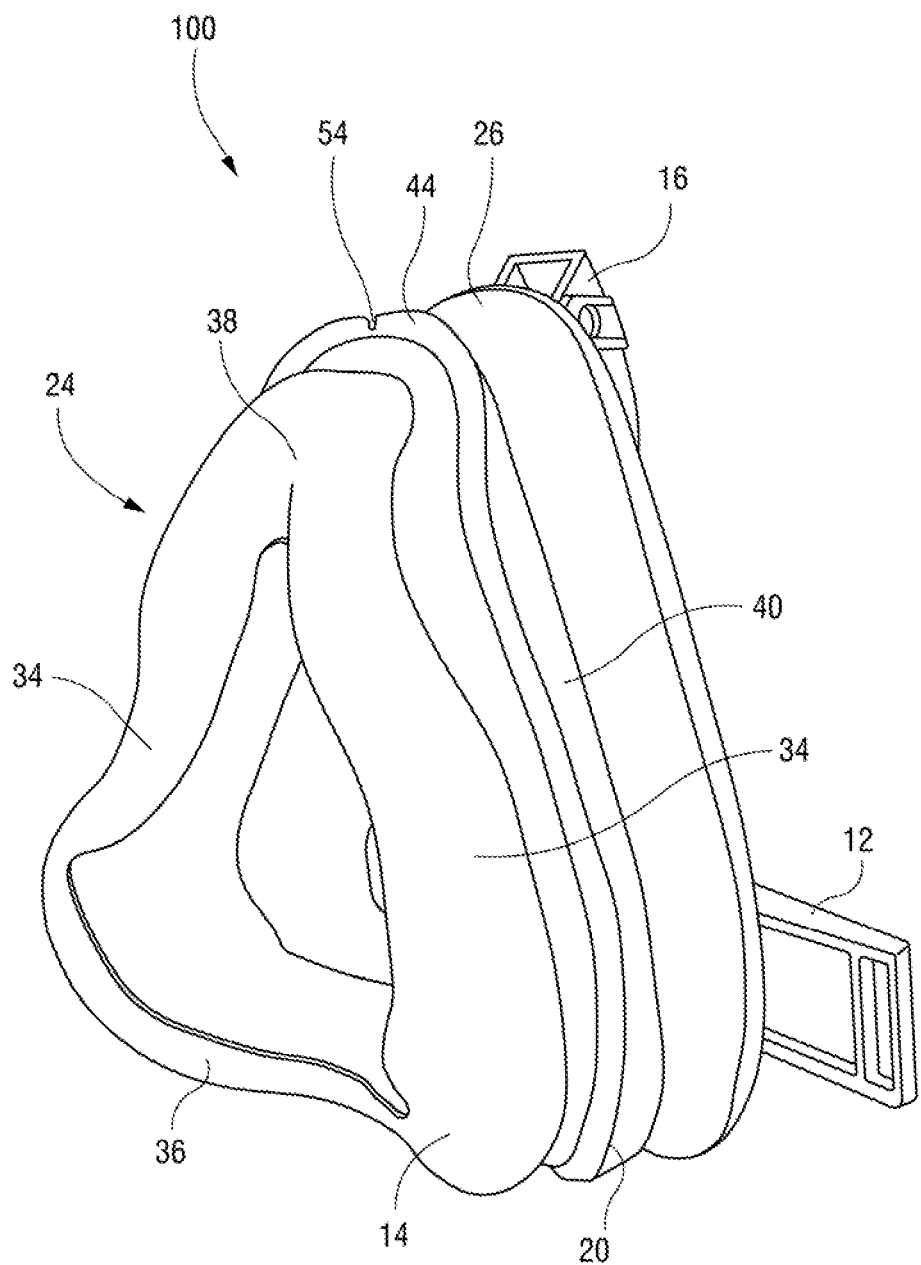

FIGS. 1-2 illustrate an embodiment of a patient interface 100 that is structured to deliver breathable gas to a patient. The patient interface 100 includes a frame 12 and a cushion 14 that may be permanently or removably connected to the frame 12. A forehead support may be movably mounted to an upper portion 16 of the frame 12. A headgear assembly (not shown) can be removably attached to the frame 12 to maintain the frame 12 and cushion 14 in a desired position on the patient's face. Also, a swivel elbow assembly 18 is attached to a front portion of the frame 12. The elbow assembly 18 is structured to be connected to a conduit that is connected to a pressurized supply of breathable gas. Further, a reinforcing member 20 constructed according to an embodiment of the present invention is provided on the cushion 14. As discussed below, the reinforcing member 20 is structured to limit blowout or lateral expansion of the cushion 14 when subject to high pressures during use.

In the illustrated embodiment, the patient interface 100 is a full-face mask structured to deliver breathable gas to a patient's nose and mouth. However, the patient interface 100 may be a nasal mask, an oro-nasal mask, a mouth mask, nasal prongs, etc.

Figure 3:
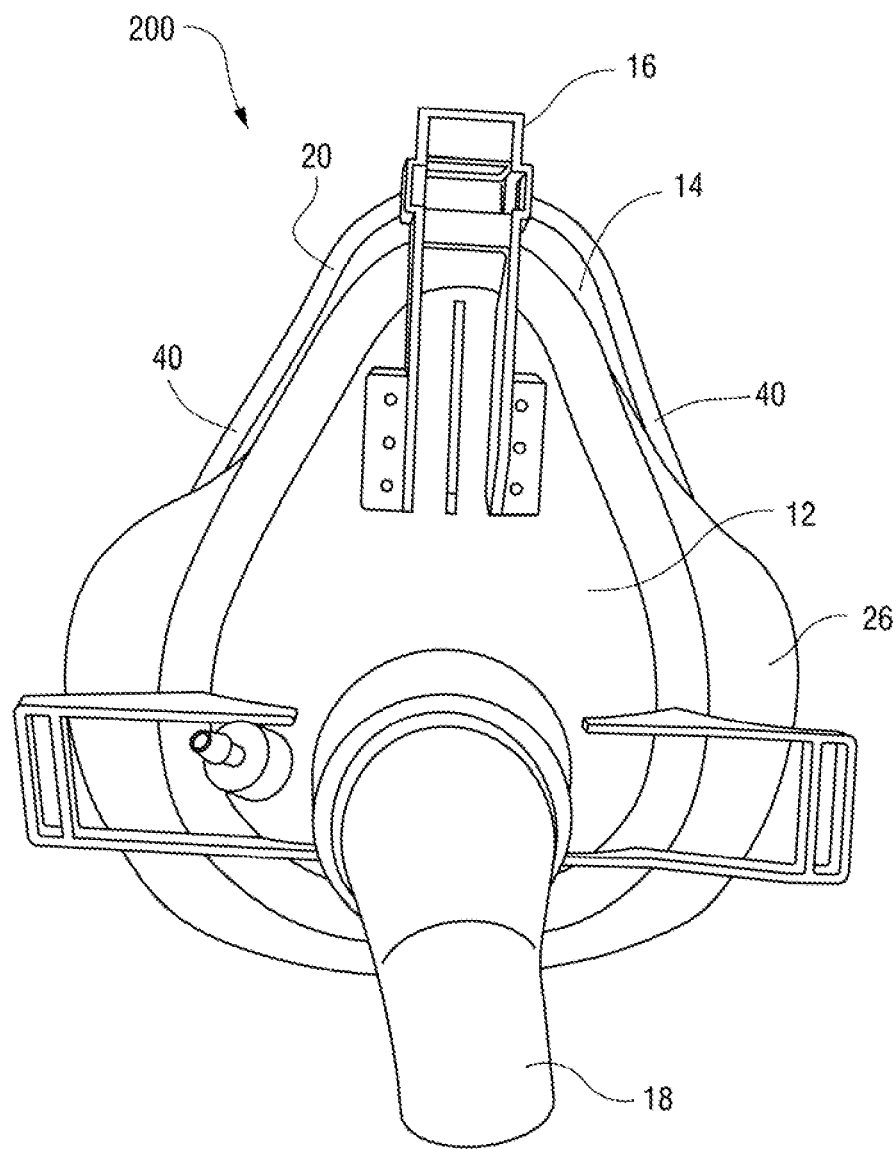
FIGS. 3-5 illustrate a patient interface including a reinforcing member constructed according to another embodiment of the present invention.
Figure 4:
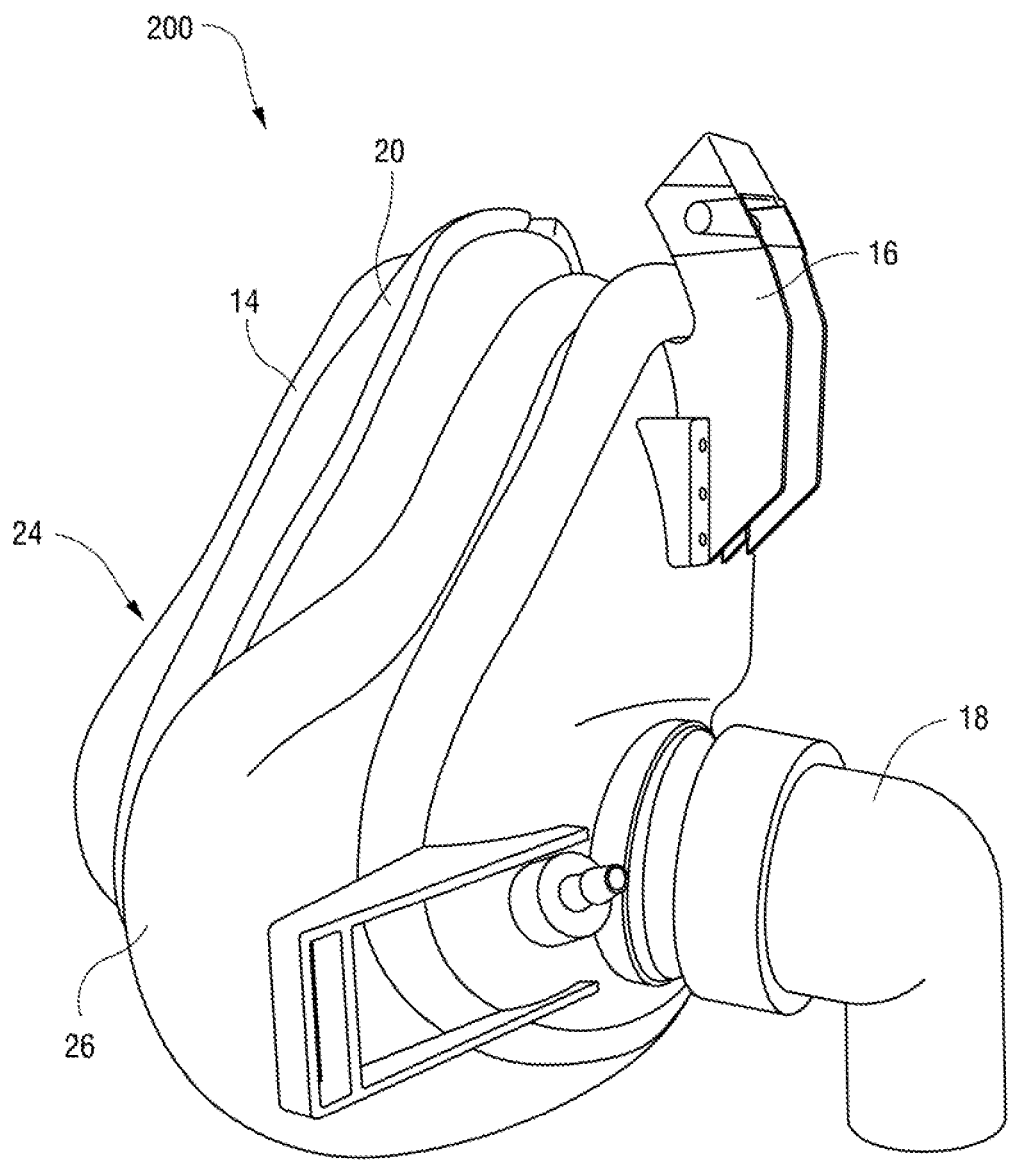
Figure 5:
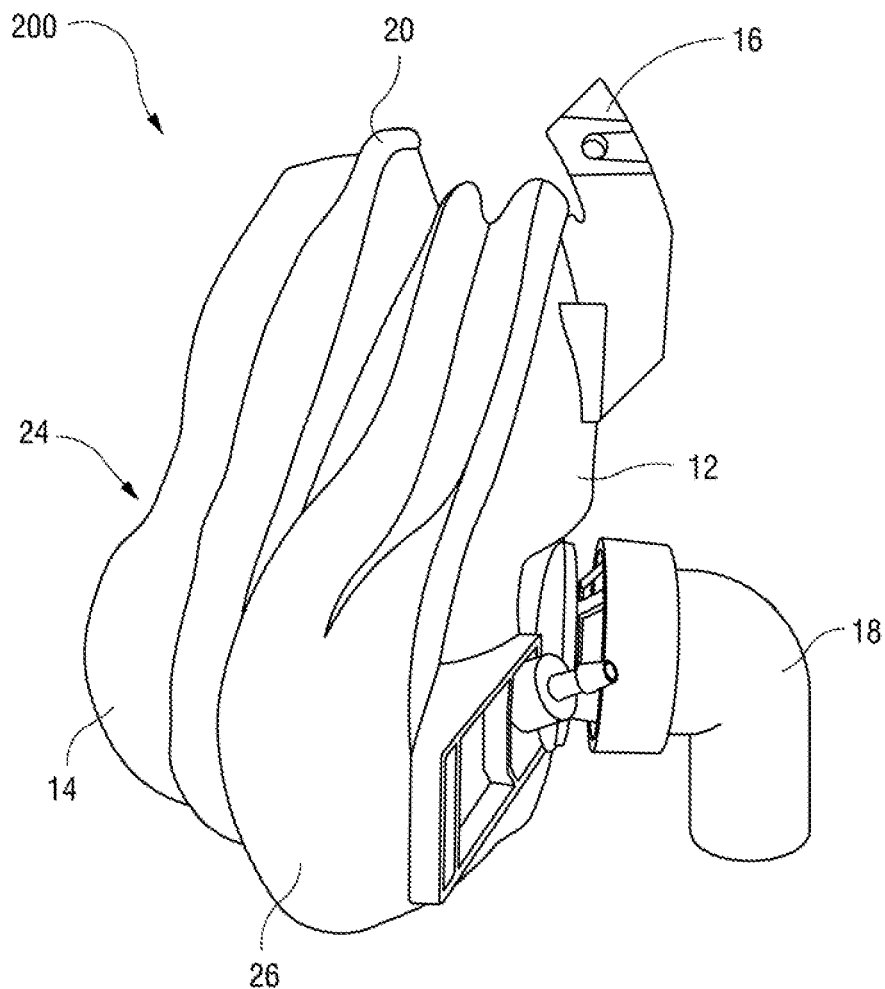
Figure 6:
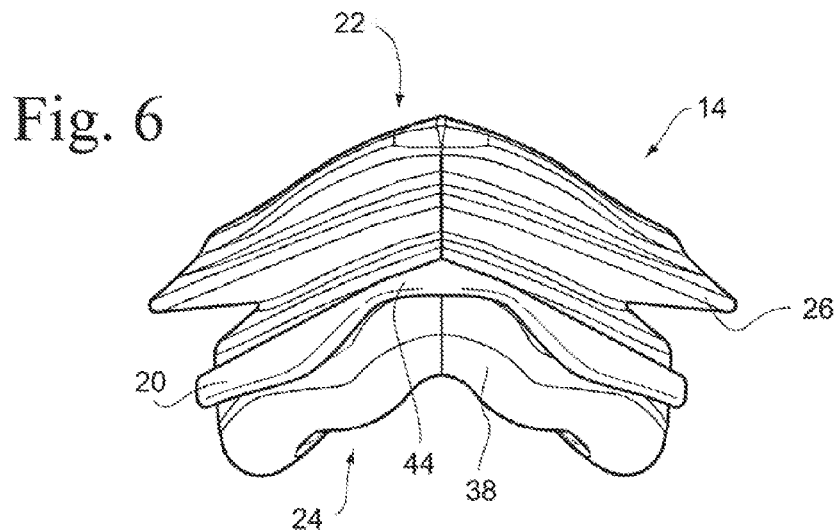
FIGS. 6-8 illustrate a cushion of a patient interface including a reinforcing member constructed according to another embodiment of the present invention.
Figure 7:
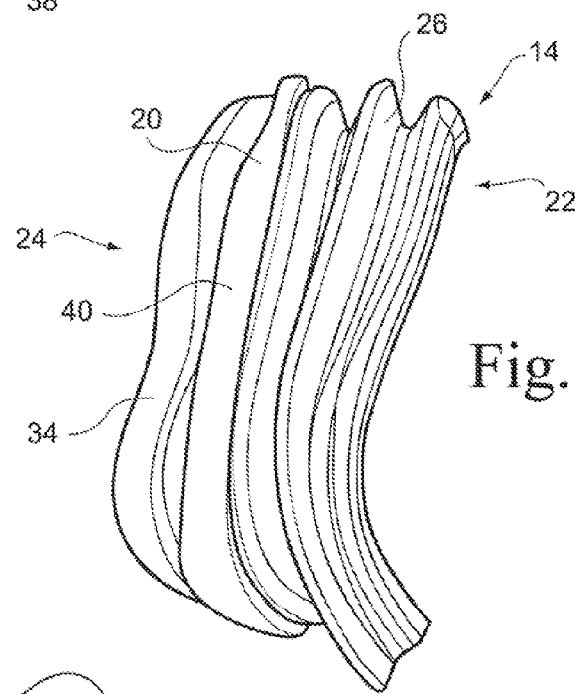
Figure 8:
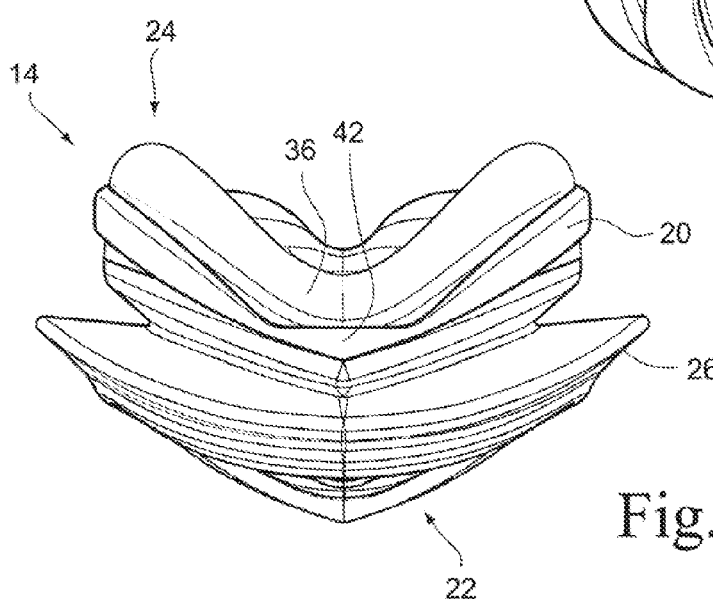

FIGS. 3-5 illustrate another embodiment of a patient interface 200 with a reinforcing member 20 attached thereto, and FIGS. 6-8 illustrate another embodiment of a cushion 14 with a reinforcing member 20 attached thereto. Similar elements are indicated with similar reference numerals in the figures. These embodiments primarily differ in the configuration of the gusset portion 26 of the cushion 14, although it should be noted that the reinforcing member 20 also has application to masks not including gussets.

As best shown in FIGS. 9-23, the cushion 14 includes a non-face-contacting portion 22 structured to be connected to the frame 12, e.g., via a tongue-and-groove arrangement, a face-contacting portion 24 structured to engage a patient's face, and a gusset portion 26 that interconnects the non-face contacting portion 22 and the face-contacting portion 24. As illustrated, a preferred face-contacting portion 24 of the cushion 14 includes a side wall 28, an underlying cushion 30 extending away from the side wall 28, and a membrane 32 provided to substantially cover at least a portion of the underlying cushion 30, e.g., see U.S. Pat. No. 6,112,746 of Kwok et al. and U.S. patent application Ser. No. 10/390,682, each incorporated herein by reference in its entirety.

Figure 9:
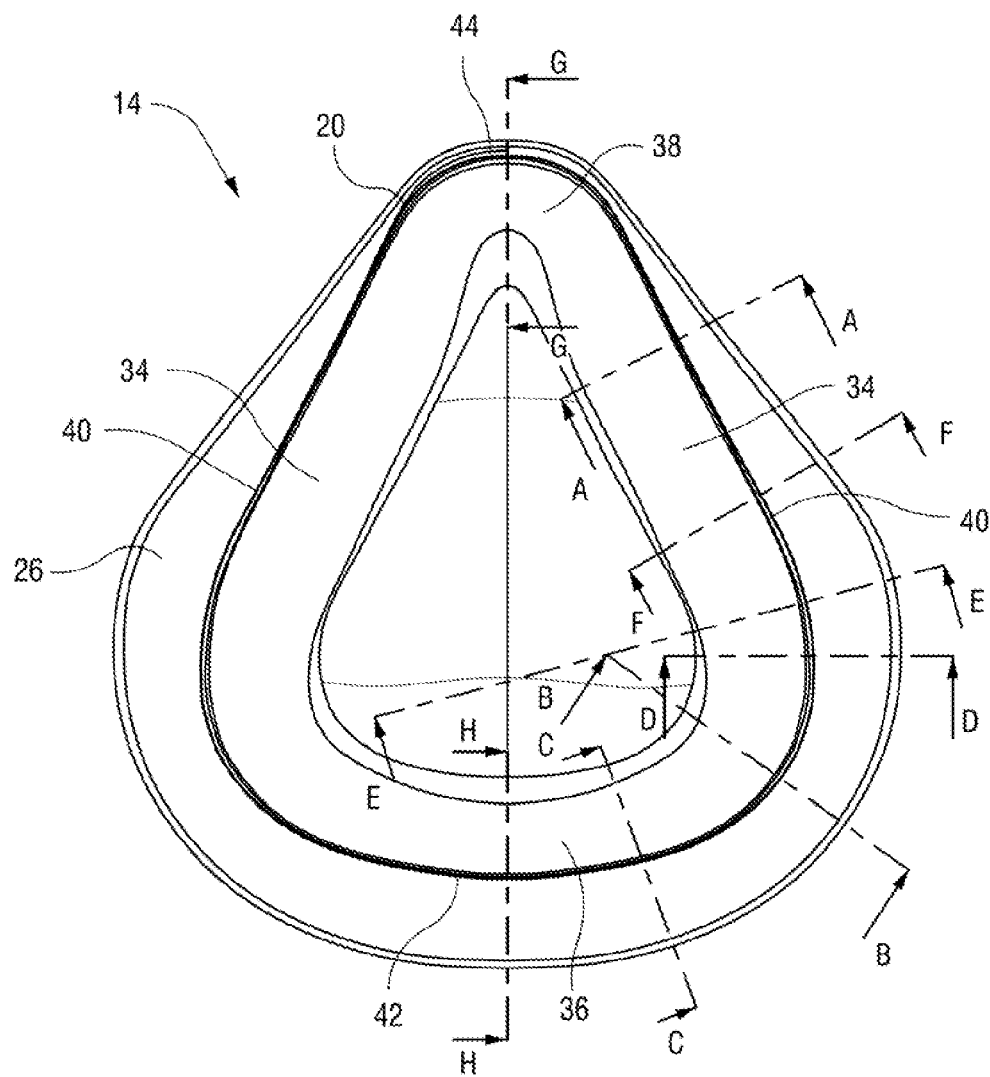

As best shown in FIG. 9, the face-contacting portion 24 of the cushion 14 preferably has a generally triangular shape and is structured to contact the nasal bridge, cheek, and lower lip region of the patient. However, the face-contacting portion 24 may have any other suitable shape, e.g., a generally trapezoidal shape. In the illustrated embodiment, the cushion 14 includes a pair of cheek regions 34 to provide a seal along the cheeks and the sides of the mouth, a lower lip region 36 to provide a seal below the lower lip of the patient, and a nasal bridge region 38.

The gusset portion 26 extends radially outwardly with respect to the non-face-contacting and face-contacting portions 22, 24, which allows the face-contacting portion 24 to move relative thereto. The gusset portion 26 also increases the sealing efficiency of the cushion 14. Further details of gusset portions 26 are disclosed in U.S. patent application Ser. No. 10/655,622 and U.S. Pat. No. 6,772,760, each incorporated herein by reference in its entirety.

The gusset portion 26 may be provided in only selected regions of the face, and not others. It need not be provided along the entire perimeter of the cushion 14. Also, the width of the gusset portion 26 may vary along the perimeter of the cushion 14. For example, FIGS. 1 and 2 illustrate an embodiment wherein the width of the gusset portion 26 is substantially constant along the perimeter of the cushion 14, whereas FIGS. 3-5 and 9 illustrate embodiment wherein the width of the gusset portion 26 is wider in selected regions of the cushion 14, e.g., cheek, lower lip.

FIGS. 24-29 illustrate an embodiment of the reinforcing member 20 removed from the cushion 14, in isolation. As illustrated, the reinforcing member 20 has a ring-like structure and has a shape, e.g., generally triangular, which corresponds with the shape of the cushion 14. The reinforcing member 20 includes a pair of cheek regions 40, a lower lip region 42, and a nasal bridge region 44. In its operative position, the reinforcing member 20 engages the cushion 14 along the side wall 28 between the face-contacting portion 24 and the gusset portion 26, e.g., see FIGS. 10-17.

The reinforcing member 20 has a stiffness that may be selectively varied along its length. As shown in FIGS. 9-17, the width, depth, or transverse cross-sectional size of the reinforcing member 20 may vary along its length or perimeter to modify the stiffness or flexibility of the cushion 14 in certain regions and/or to accommodate for the relative size of the portion of the cushion 14 to be supported. That is, the reinforcing member 20 may be wider in some regions and thinner in other regions. Moreover, the variation of the width of the reinforcing member 20 may correspond with the variation of the width of the gusset portion 26 and/or the side wall 28 along its perimeter.

For example, the reinforcing member 20 is thinner in the nasal bridge region 44 and lower lip regions 42 (as best shown in FIGS. 10, 16, and 17), and the reinforcing member 20 is wider in the cheek regions 40 (as best shown in FIGS. 11-15). When attached to the cushion 14, the reinforcing member 20 is wider at the cheek regions 34 of the cushion 14 to provide more stiffness/reinforcement to the cushion 14 in this region where blowout is more likely to occur, and the reinforcing member 20 is thinner in the nasal bridge and lower lip regions 38, 36 of the cushion 14 to provide less stiffness/reinforcement to the cushion 14 where blowout is less likely to occur. However, the width of reinforcing manner 20 may be varied around its perimeter in any suitable manner. Moreover, the reinforcing member 20 may have a substantially constant width, height, or cross-sectional profile around its perimeter.

Also, the reinforcing member 20 may be suitably structured such that it can be used with different embodiments and sizes of patient interfaces. Further, the reinforcing member 20 may be suitably structured based on particular needs of a patient. For example, the size of the reinforcing member 20 may be suitably varied based on the treatment pressure that the patient typically experiences.

FIGS. 18-23 illustrate various embodiments of attaching the reinforcing member 20 to the cushion 14. For example, FIG. 18 illustrates an embodiment of a pair of spaced apart reinforcing members 20a, 20b attached, e.g., by friction fit, to an exterior surface of the side wall 28 of the cushion 14. FIG. 19 illustrates an embodiment of a reinforcing member 20 that is received within a channel 46 provided around at least a portion of the exterior surface of the side wall 28 of the cushion 14. FIG. 20 illustrates an embodiment of a reinforcing member 20 having a stepped cross-section configuration around at least a portion thereof that is received within a complementary shaped groove 48 provided around at least a portion of the exterior surface of the side wall 28 of the cushion 14. FIG. 21 illustrates an embodiment of a reinforcing member 20 that is received within a channel 46 provided around at least a portion of the interior surface of the side wall 28 of the cushion 14. FIG. 22 illustrates an embodiment of a reinforcing member 20 that is attached to the exterior surface of the side wall 28 of the cushion 14 by mechanical fasteners 50, e.g., screws. FIG. 23 illustrates an embodiment of a reinforcing member 20 that is attached to the exterior surface of the side wall 28 of the cushion 14 by an adhesive 52, e.g., glue or ultrasonic welding or the like.

As shown in FIGS. 28 and 29, the reinforcing member 20 may have a curved or arcuate-shaped transverse cross-sectional configuration. The cushion 14 may have a complementary shaped recess adapted to receive the curved reinforcing member 20 therein with an interference fit.

However, it should be understood that the reinforcing member 20 may be secured to the cushion 14 in any other suitable manner. Moreover, the reinforcing member 20 may be secured using combinations of the attaching embodiments described above.

As shown in FIG. 2, the reinforcing member 20 may include a gap 54 in the nasal bridge region 44. The gap 54 may be provided to allow for more movement/flexibility in the nasal bridge region 44, or to facilitate assembly of the reinforcing member 20 to the cushion 14.

To better understand the advantages of the present invention, a coordinate system is defined with respect to the facial profile of a patient. When a patient is sitting upright, the x-axis is horizontal, the y-axis is vertical, and the z-axis is into the plane of the patient's face. The reinforcing member 20 adds stiffness to the cushion 14 in the x-y plane to limit lateral expansion of the cushion 14, referred to as blowout, when subject to high pressures. The reinforcing member 20 also adds stiffness to the cushion 14 in the y-z plane. That is, the reinforcing member 20 links the top and bottom of the cushion 14 which limits independent movement of the top and bottom of the cushion 14 towards and away from the patient's face, i.e., along the z-axis. The reinforcing member 20 helps the cushion move in a more uniform manner along the z-axis. Thus, the reinforcing member 20 provides both lateral support and z-axis support to improve the stability of the cushion 14.

Also, the reinforcing member 20 may beneficially add mass to the cushion 14 which may improve stability by allowing the cushion 14 to slowly adapt to changes in pressure. That is, the added mass of the reinforcing member 20 may slow the movement of the cushion 14 as it extends and retracts away and towards the patient's face during use.

In illustrated embodiments, the reinforcing member 20 is formed separately from the cushion 14 and attached thereto. The reinforcing member 20 may be constructed of a suitable substantially rigid material, e.g., plastic, composite, etc. However, in other embodiments, the reinforcing member 20 may be overmolded onto the cushion 14 to form an integral structure. In one example, the reinforcing member 20 may be embedded along at least a portion of the perimeter of the cushion 14. Also, the reinforcing member 20 may be constructed from a thickened bead of silicone that is molded with the cushion 14 as disclosed in U.S. patent application Ser. No. 10/655,622, filed Sep. 5, 2003, the entirety of which is hereby incorporated herein by reference. In general, the reinforcing member 20 is rigid relative to the cushion 14 under pressure.

In another embodiment, ribs and/or additional thickness may be added to the side wall 28 of the cushion 14 in lieu of the reinforcing member 20. The ribs and/or thickness would perform the same function of stiffening the side wall 28 of the cushion 14 to prevent blowout. In an alternative embodiment, the ribs and/or additional thickness may be utilized in combination with the reinforcing member 20.

In another embodiment, a spring, screw thread, or clipping arrangement, for example, may be incorporated into the reinforcing member 20 to allow the reinforcing member 20 to be resized according to the cushion size or pressure range for which it will be used.

Figure 30:
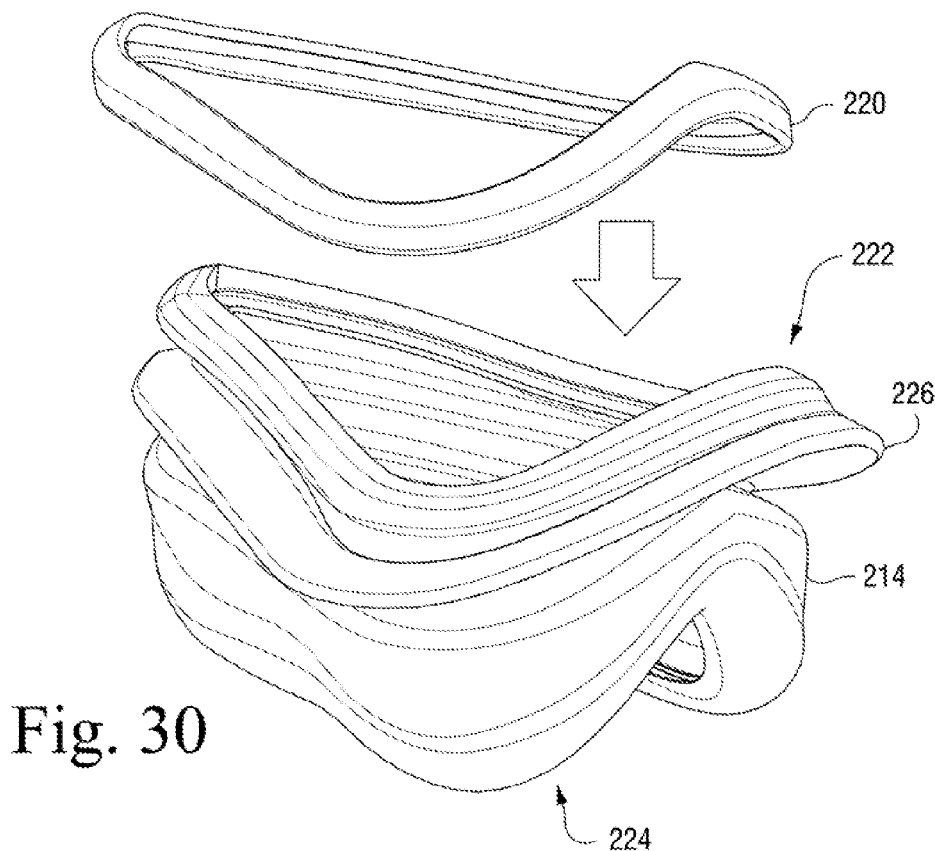
FIGS. 30-38 illustrate a cushion of a patient interface including a reinforcing member constructed according to another embodiment of the present invention.
Figure 31:
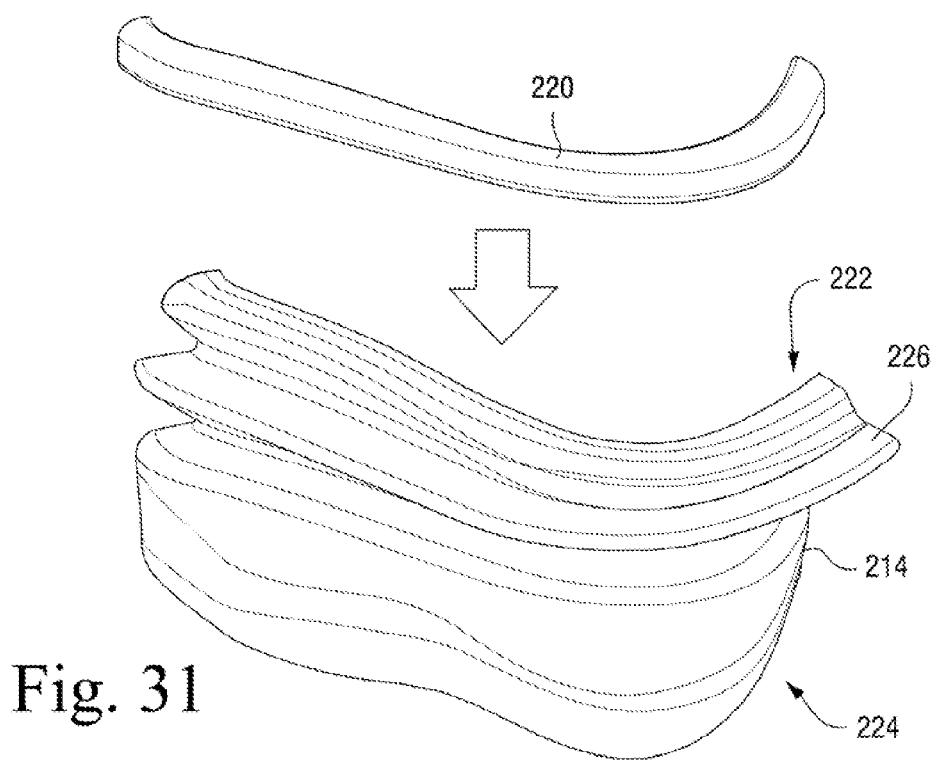
Figure 32:
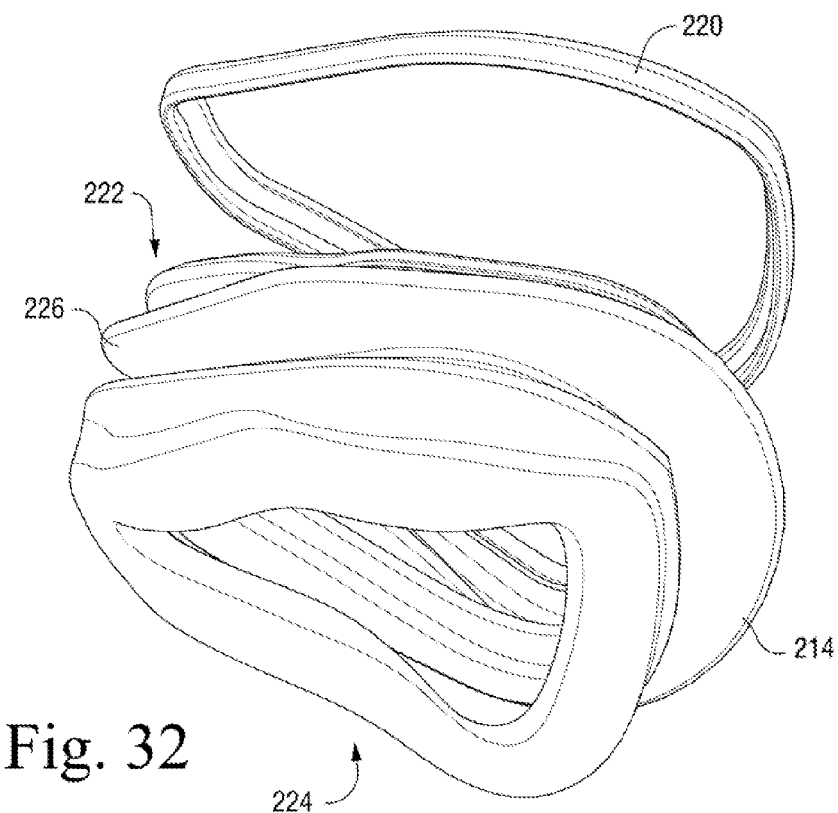
Figure 33:
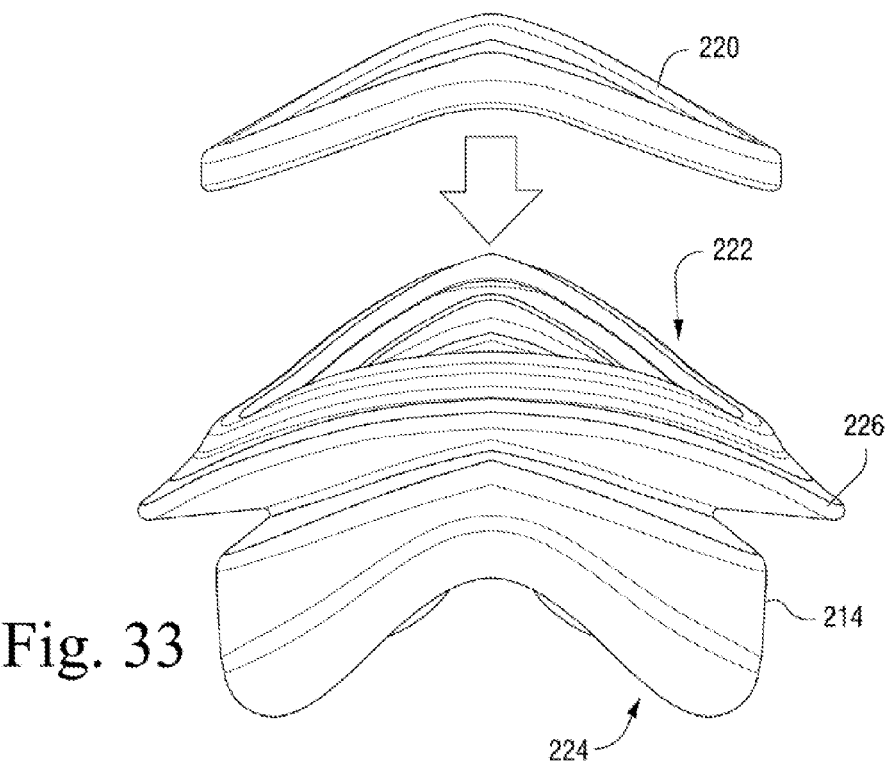
Figure 34:
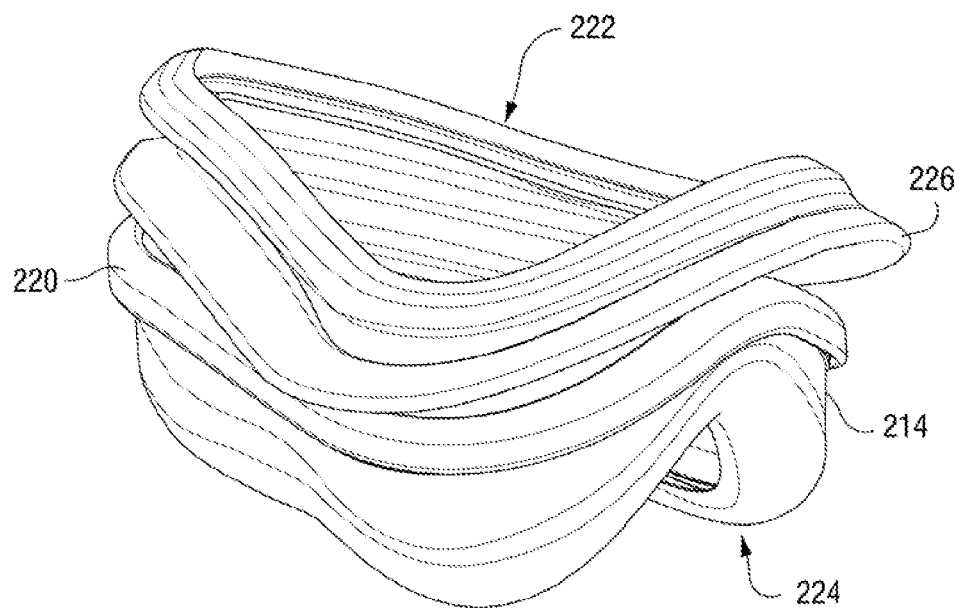
Figure 35:
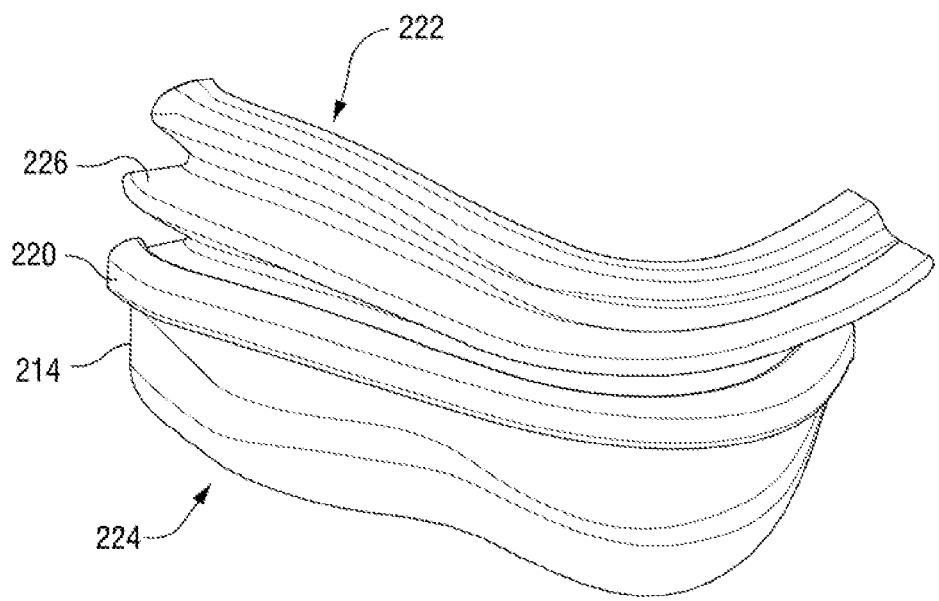
Figure 36:
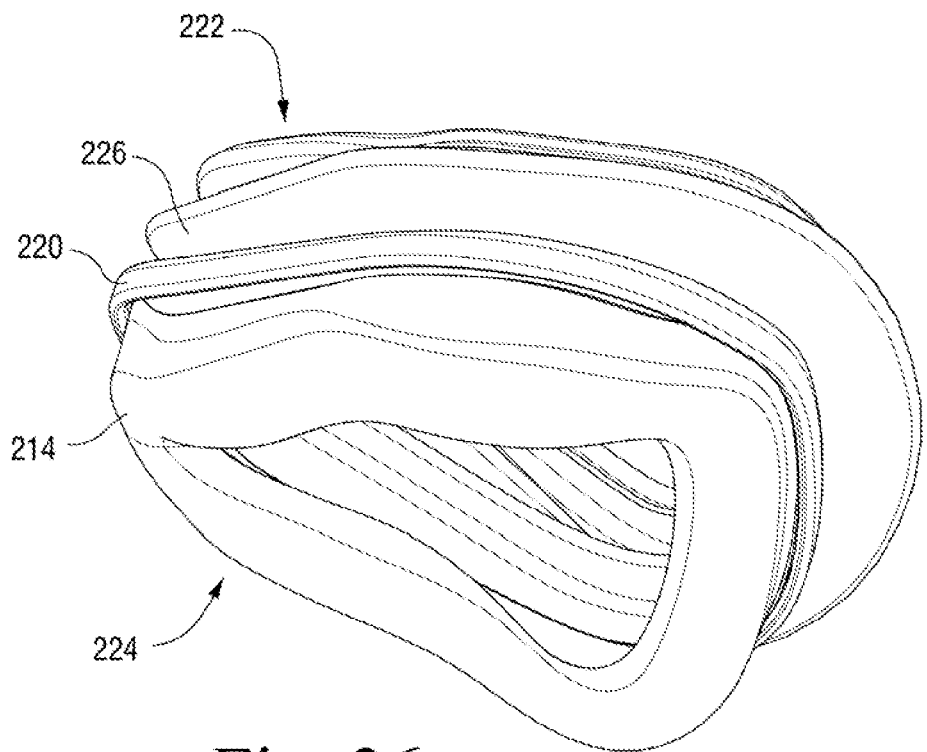
Figure 37:
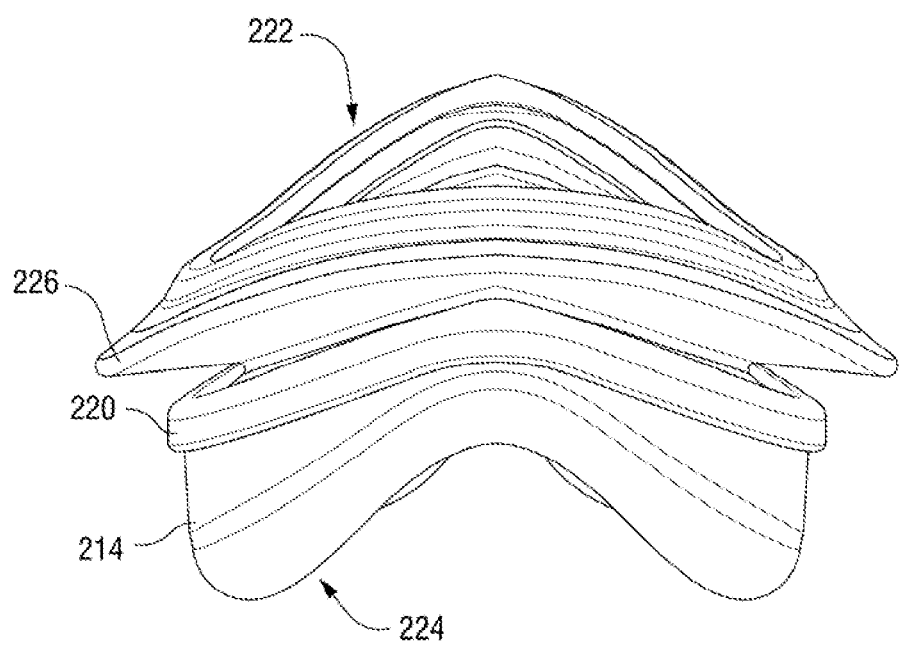
Figure 38:
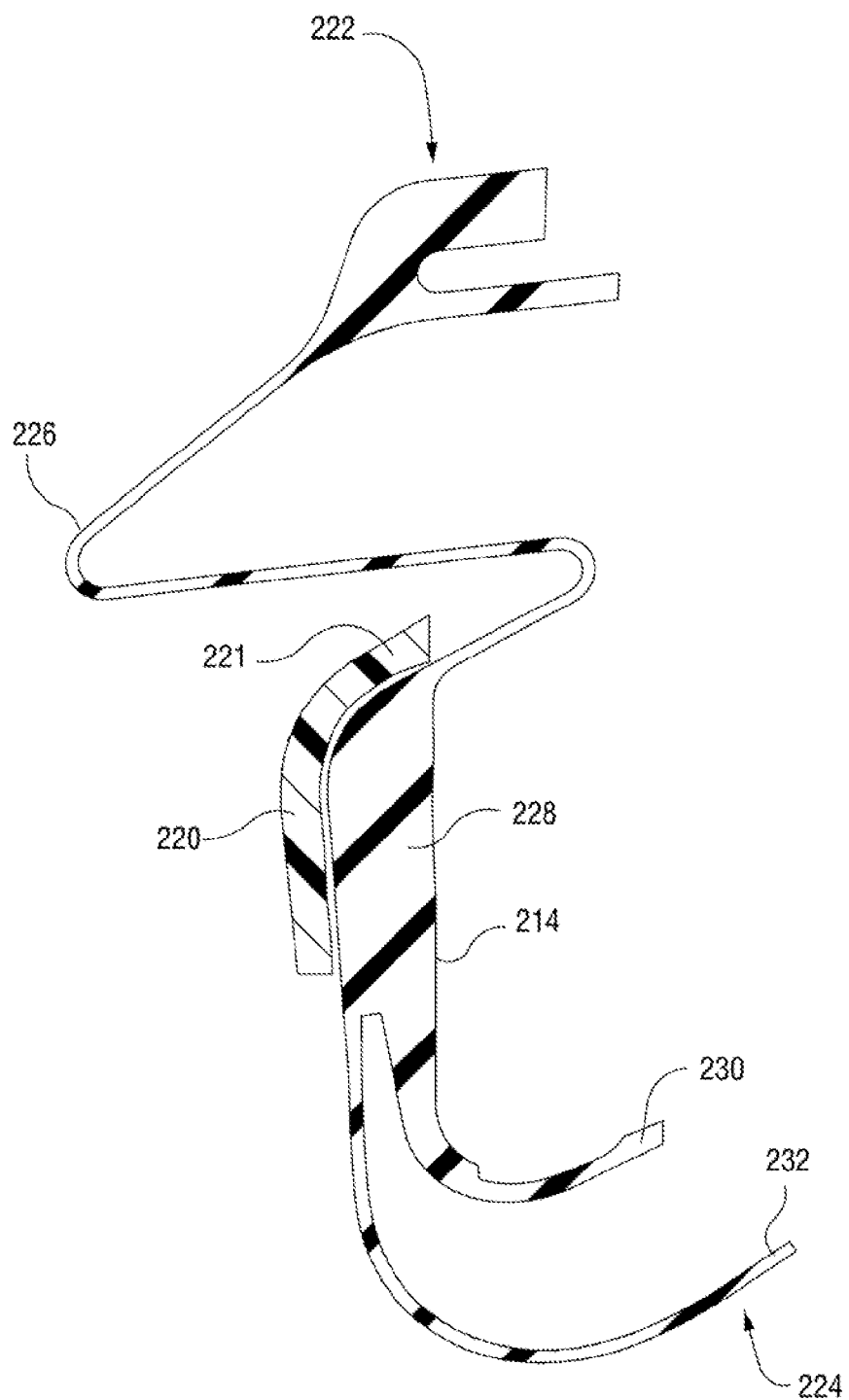
Figure 39:
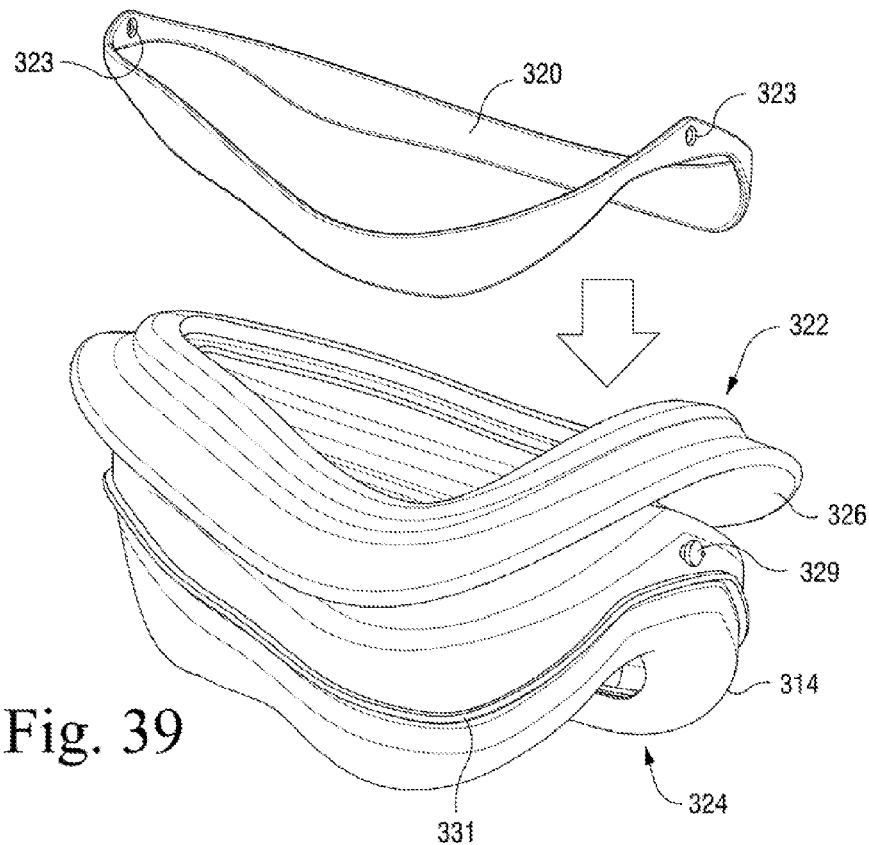
FIGS. 39-47 illustrate a cushion of a patient interface including a reinforcing member constructed according to another embodiment of the present invention.
Figure 40:
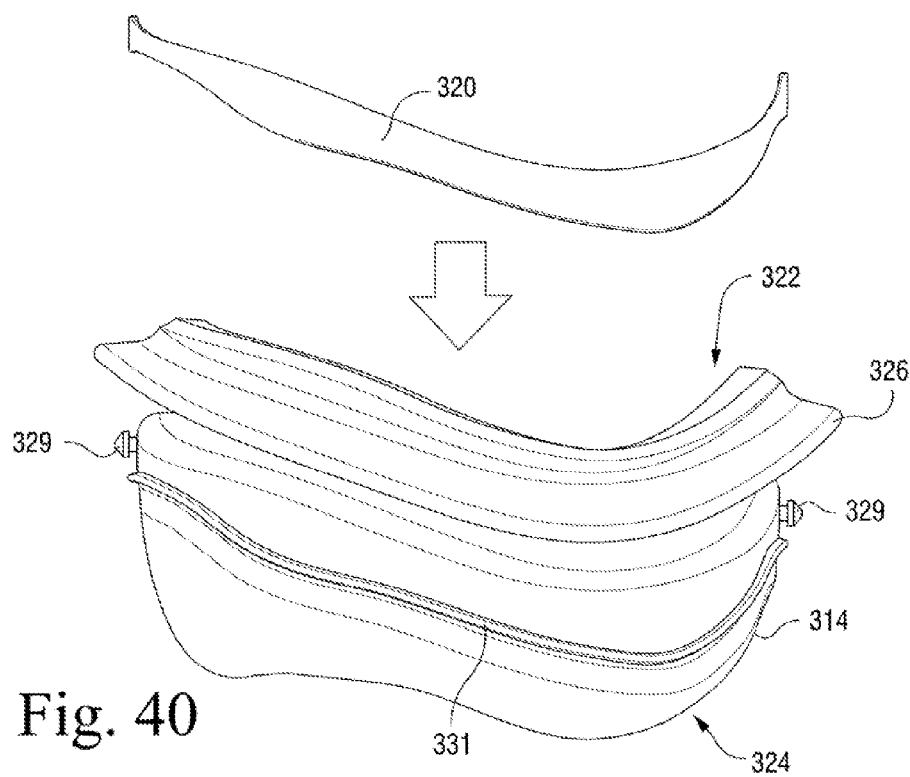
Figure 41:
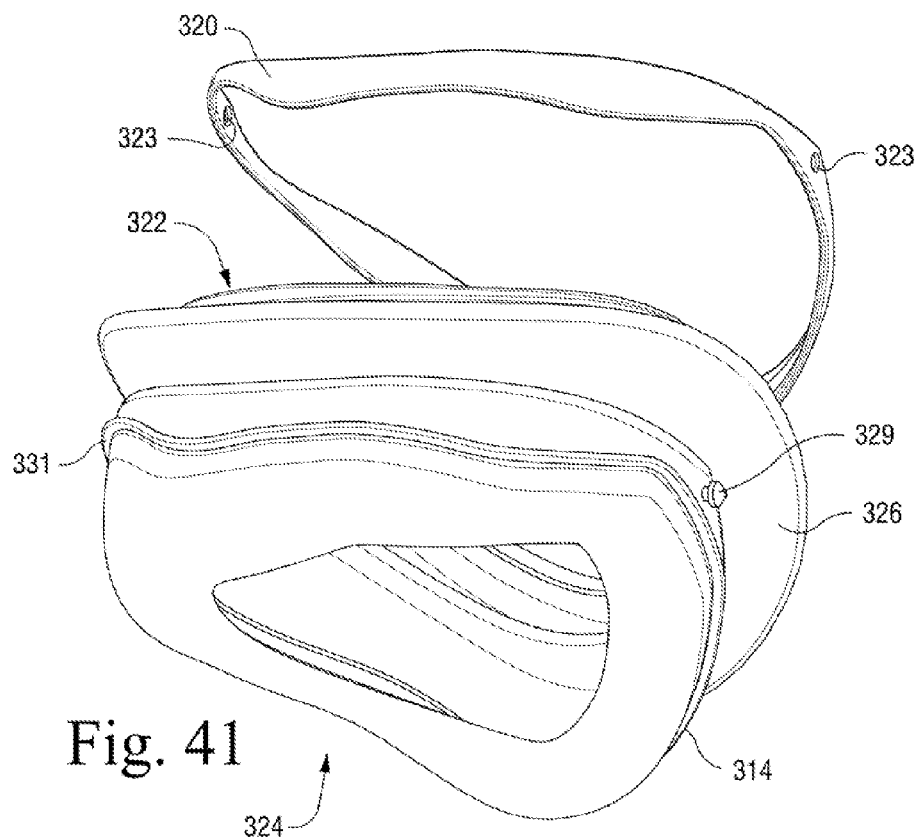
Figure 42:
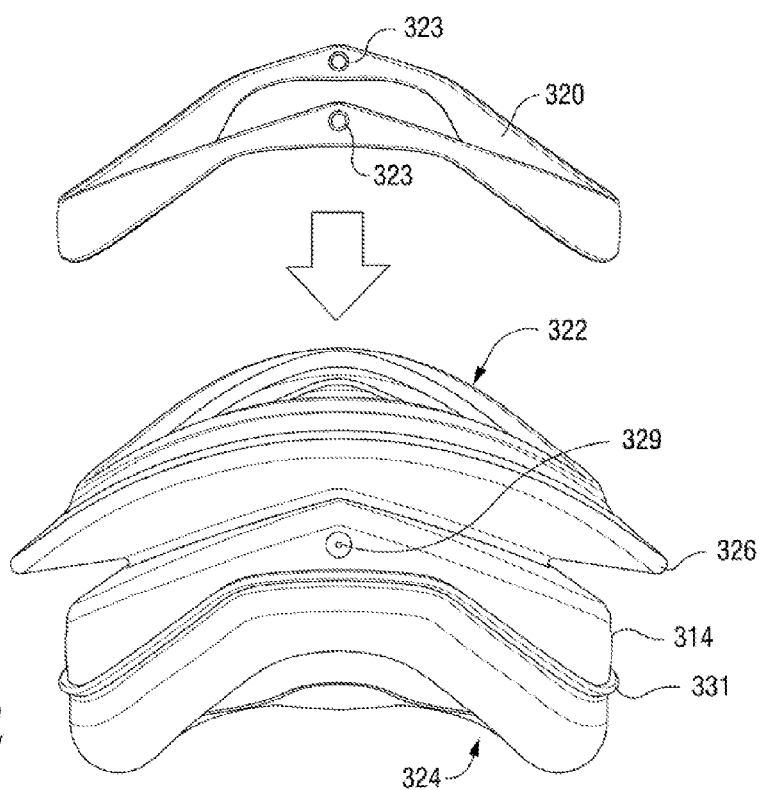
Figure 43:
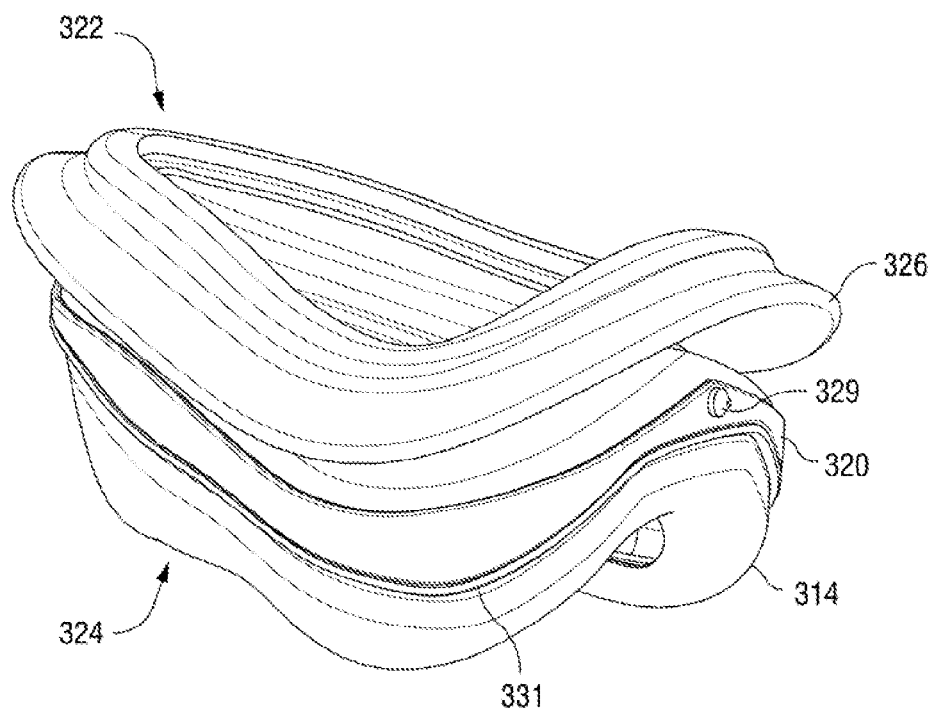
Figure 44:
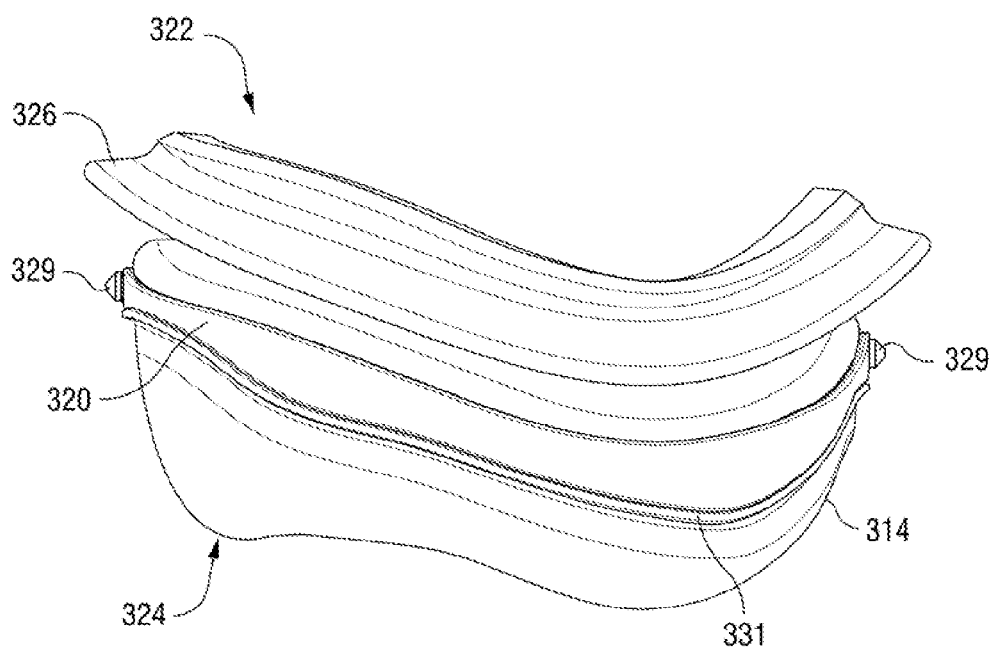
Figure 45:
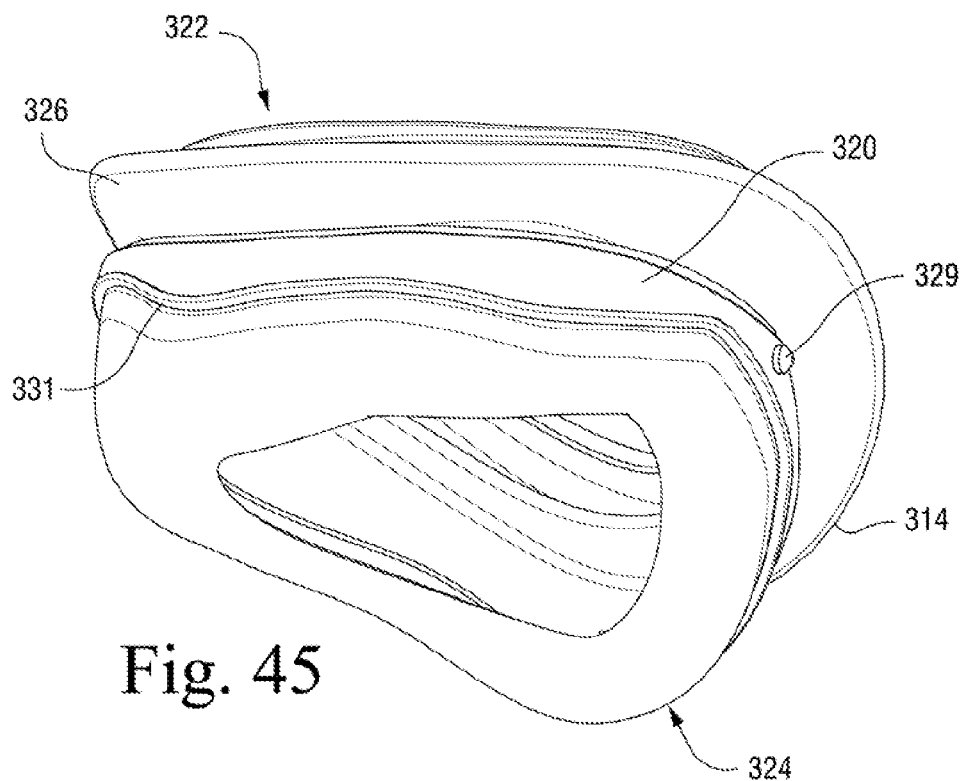
Figure 46:
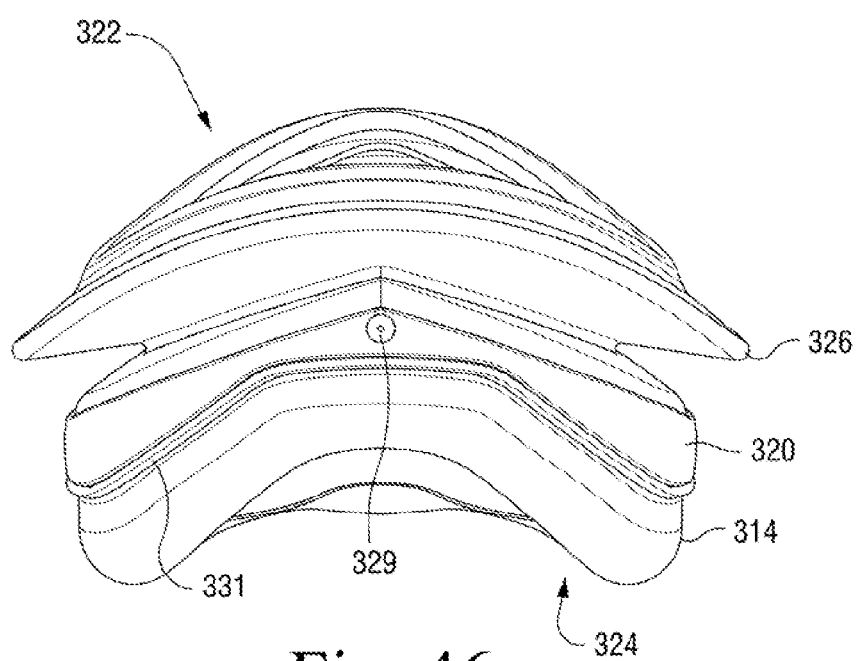
Figure 47:
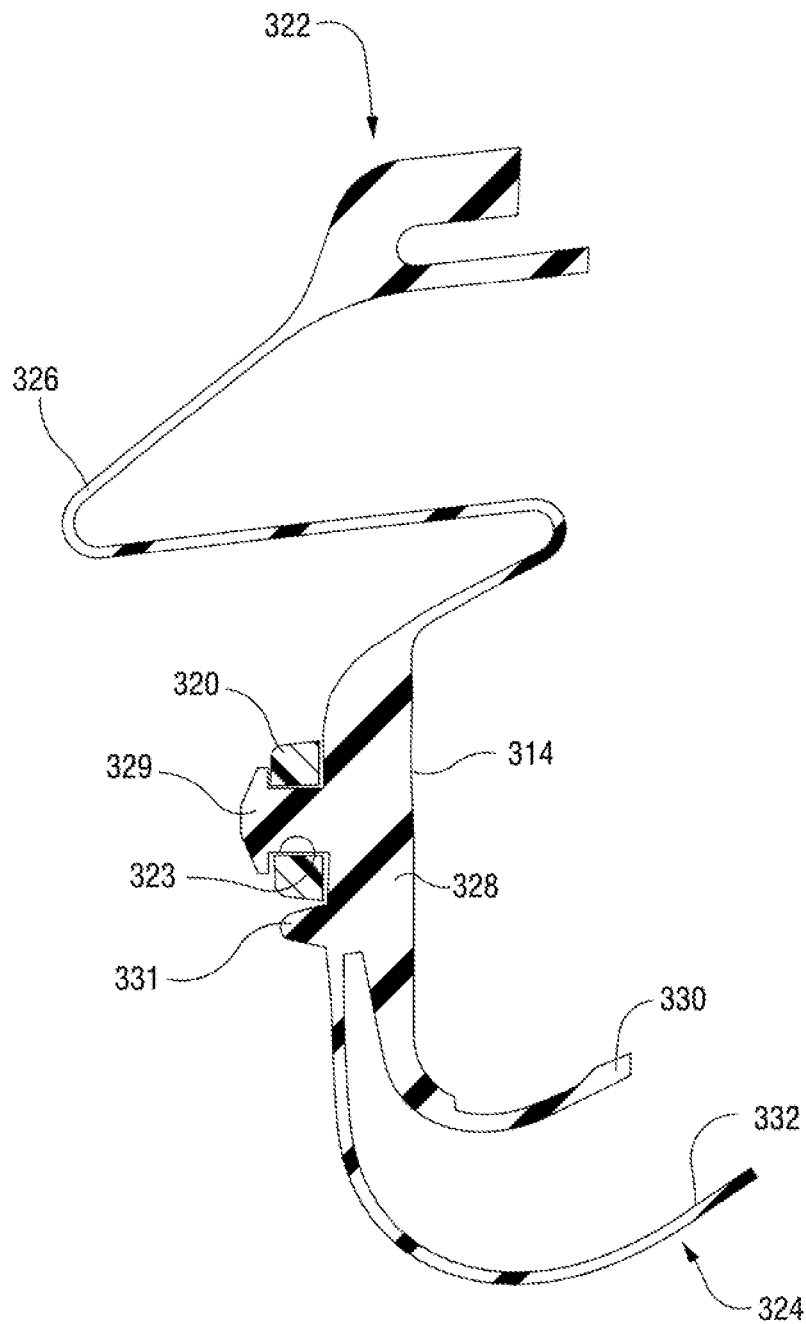
Figure 82:
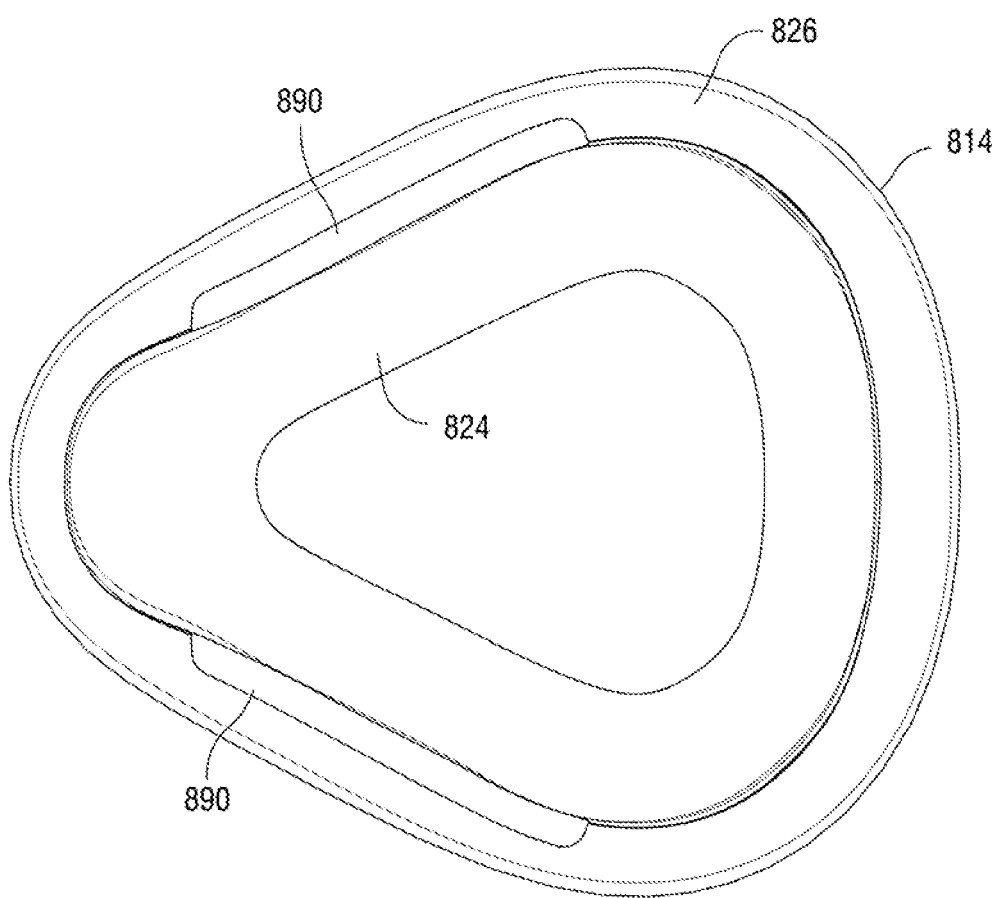

FIGS. 30-82 illustrate alternative embodiments of reinforcing members. For example, FIGS. 30-38 illustrate another embodiment of a reinforcing member 220 (also referred to as a cushion overclip or saddle overclip) provided to a cushion 214. As illustrated, the cushion 214 includes a non-face-contacting portion 222, a face-contacting portion 224, and a gusset portion 226 that interconnects the non-face contacting portion 222 and the face-contacting portion 224. The face-contacting portion 224 of the cushion 214 includes a side wall 228, an underlying cushion 230, and a membrane 232 (see FIG. 38).

As shown in FIGS. 30-33, the reinforcing member 220 assembles to the cushion 214 from the top, e.g., over the non-face-contacting portion 222. The reinforcing member 220 includes a flange 221 that assists with positioning and retention on the cushion 214 (see FIG. 38). In its operative position, the reinforcing member 220 engages the cushion 214 along the side wall 228 between the face-contacting portion 224 and the gusset portion 226, e.g., see FIGS. 34-38. The reinforcing member 220 may be glued, mechanically fastened, or overmolded in position. However, the reinforcing member 220 may be removable.

FIGS. 39-47 illustrate another embodiment of a reinforcing member 320 (also referred to as a cushion overclip or saddle overclip) provided to a cushion 314. As illustrated, the cushion 314 includes a non-face-contacting portion 322, a face-contacting portion 324, and a gusset portion 326 that interconnects the non-face contacting portion 322 and the face-contacting portion 324. The face-contacting portion 324 of the cushion 314 includes a side wall 328, an underlying cushion 330, and a membrane 332 (see FIG. 47).

The reinforcing member 320 may be assembled to the cushion 314 from the top, e.g., over the non-face-contacting portion 322, or from the bottom, e.g., over the face-contacting portion 324 (FIGS. 39-42 illustrate assembly from the top). As illustrated, the side wall 328 of the cushion 314 includes mushroom head tabs 329 integrally molded therewith. In the illustrated embodiment, the tabs 329 are provided at two positions, i.e., opposing ends of the cushion 314. However, multiple positions are possible. The tabs 329 hold the reinforcing member 320 in its operative position.

Specifically, the reinforcing member 320 includes openings 323, e.g., two openings, that receive respective tabs 329 therethrough. The tabs 329 may be pushed and/or pulled through respective openings 323 to secure the reinforcing member 320 in position. Also, the cushion 314 includes a flange 331 integrally molded therewith that assists with positioning and retention of the reinforcing member 320.

In its operative position, the reinforcing member 320 engages the cushion 314 along the side wall 328 between the face-contacting portion 324 and the gusset portion 326, e.g., see FIGS. 43-47. The reinforcing member 320 may also be glued or overmolded in position. However, the reinforcing member 320 may be removable.

Figure 48:
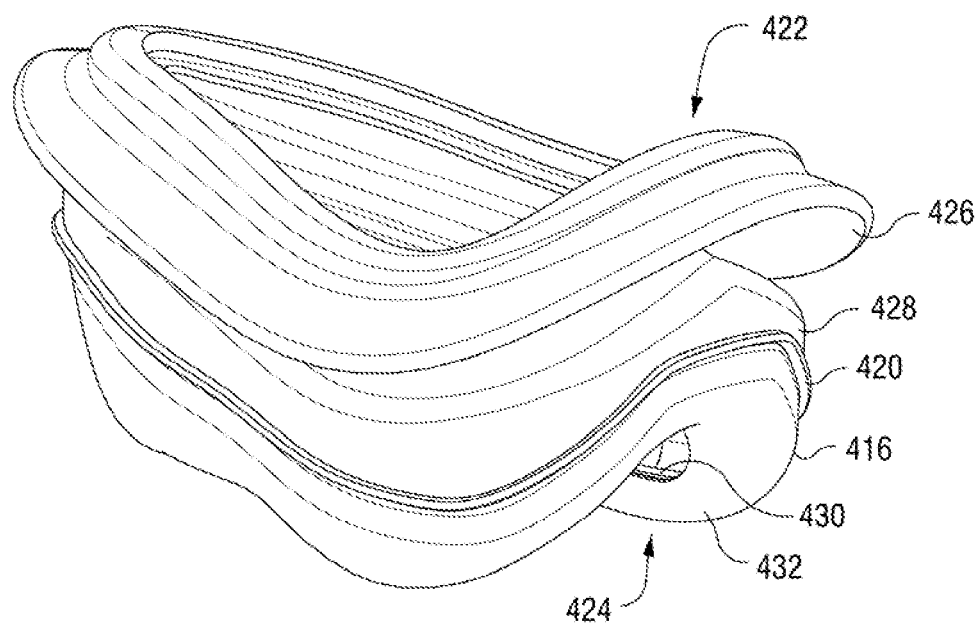
FIG. 48-49 illustrate a cushion of a patient interface including a reinforcing member constructed according to another embodiment of the present invention.
Figure 49:
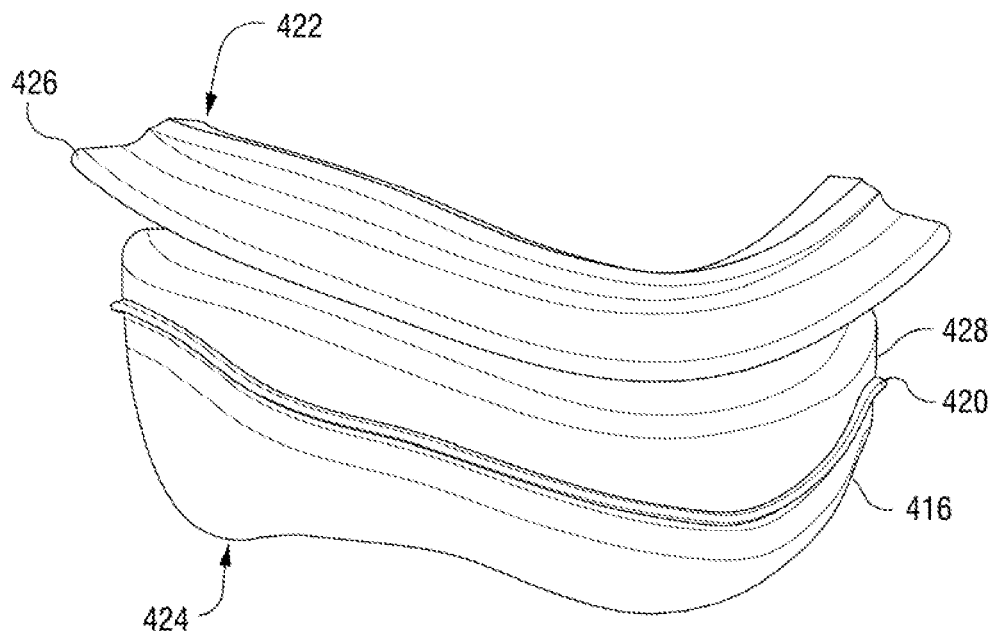

FIGS. 48-49 illustrate another embodiment of a reinforcing member 420 provided to a cushion 414. As illustrated, the cushion 414 includes a non-face-contacting portion 422, a face-contacting portion 424, and a gusset portion 426 that interconnects the non-face contacting portion 422 and the face-contacting portion 424. The face-contacting portion 424 of the cushion 414 includes a side wall 428, an underlying cushion 430, and a membrane 432.

Figure 50:
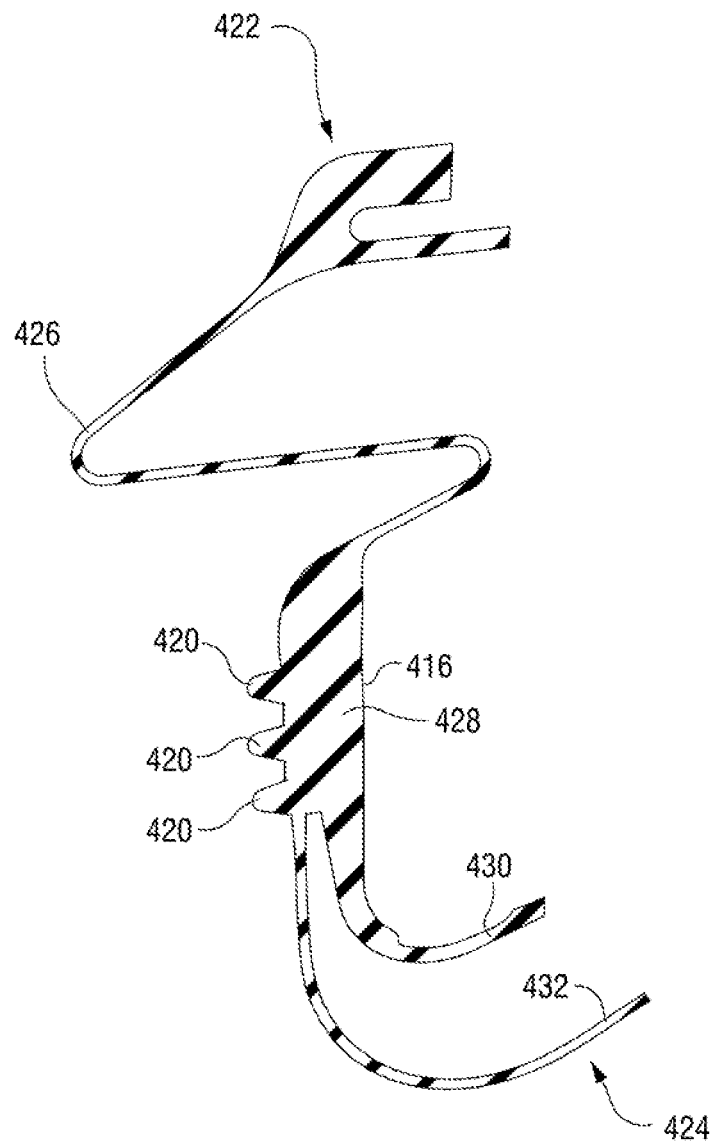
FIG. 50 illustrates a cushion of a patient interface including a reinforcing member constructed according to another embodiment of the present invention.
Figure 51:
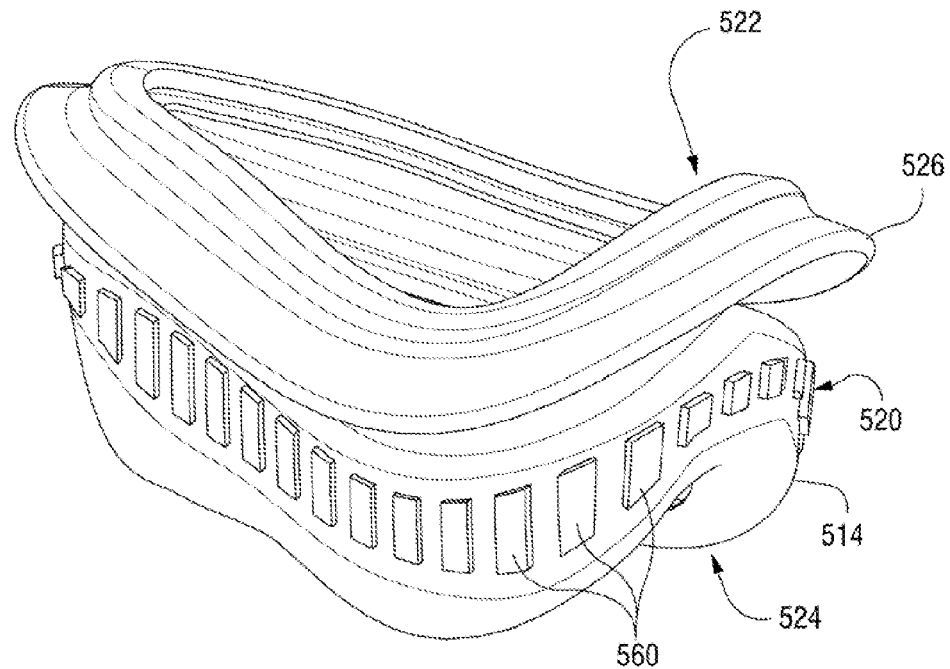
FIGS. 51-56 illustrate a cushion of a patient interface including a reinforcing member constructed according to another embodiment of the present invention.
Figure 52:
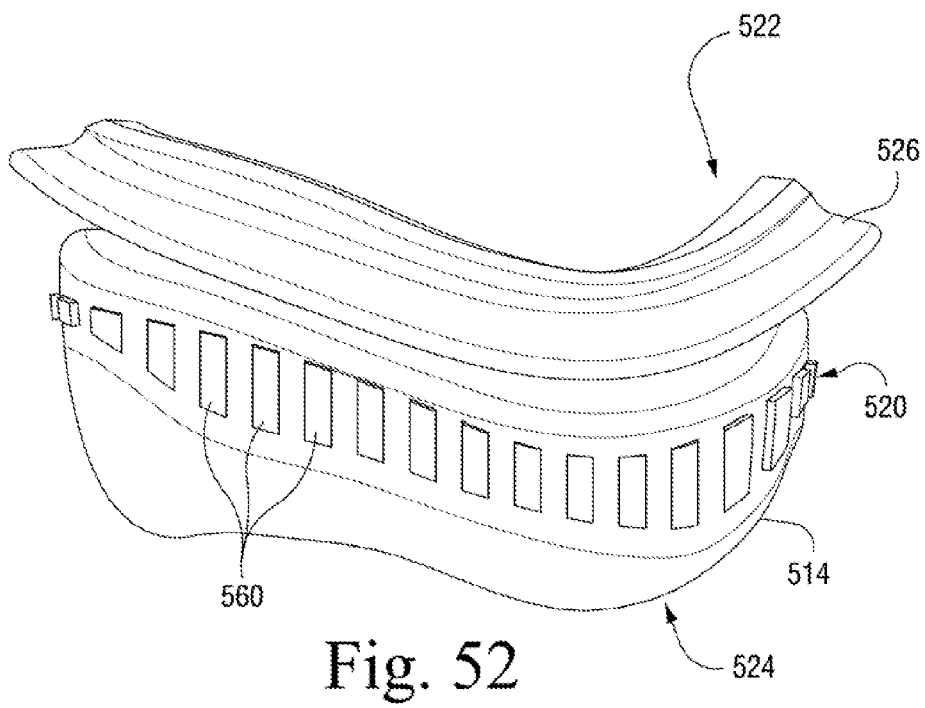
Figure 53:
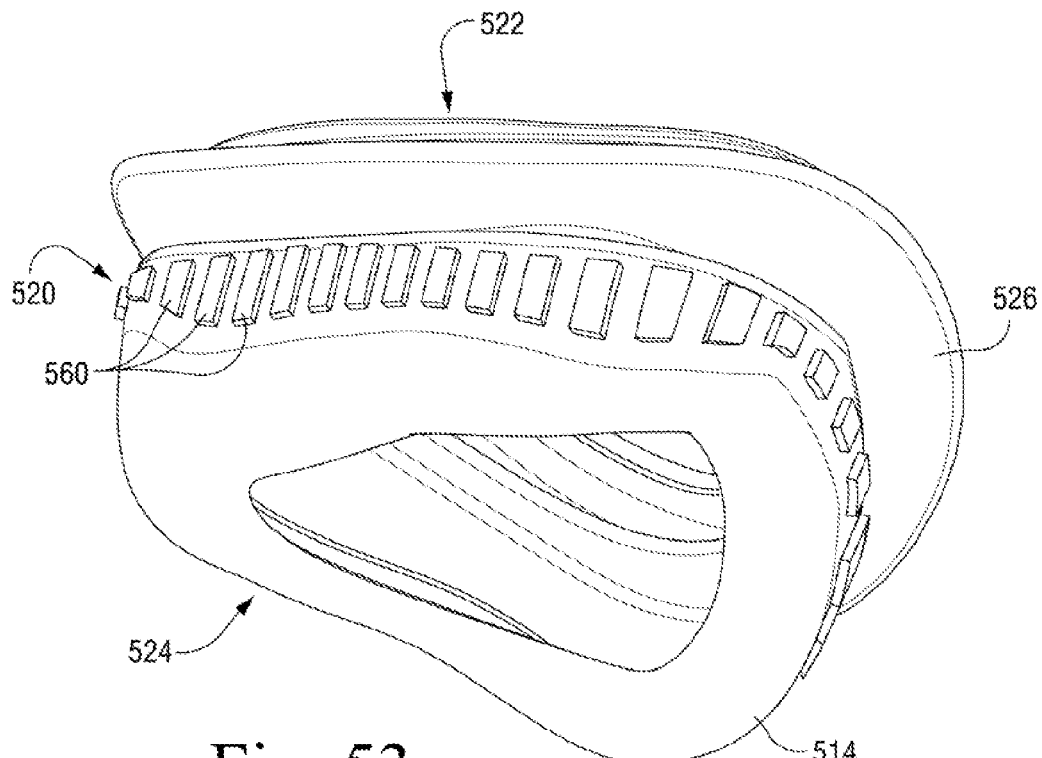
Figure 54:
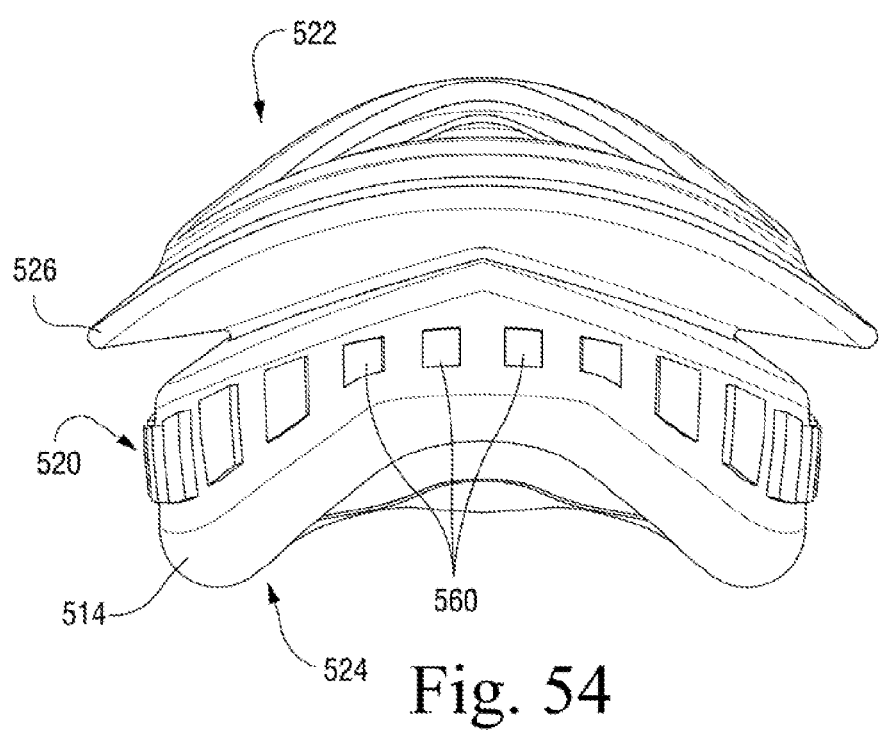
Figure 55:
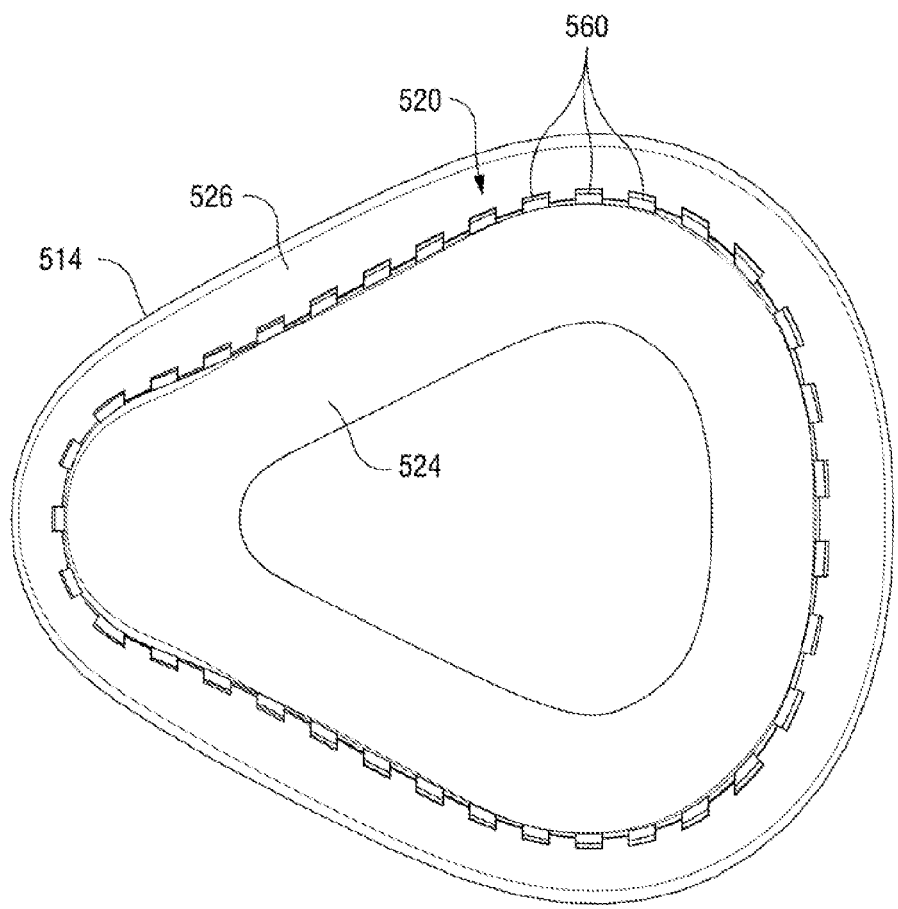
Figure 56:
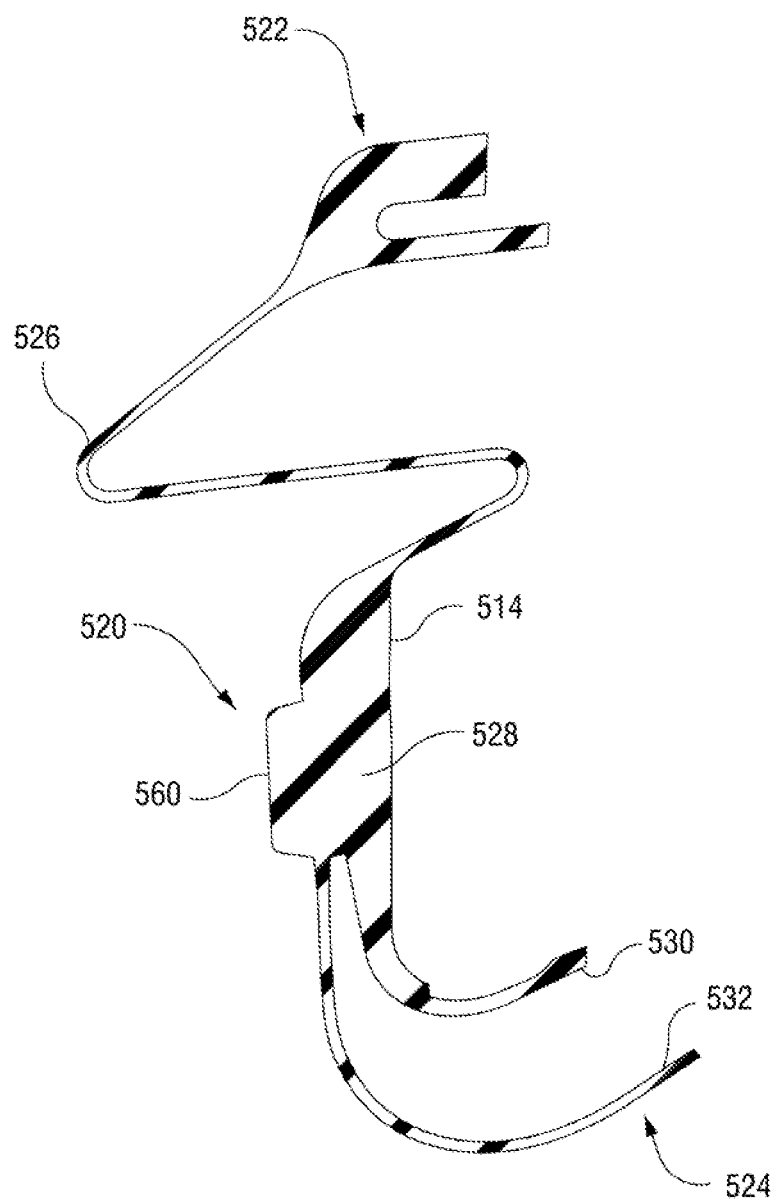
Figure 57:
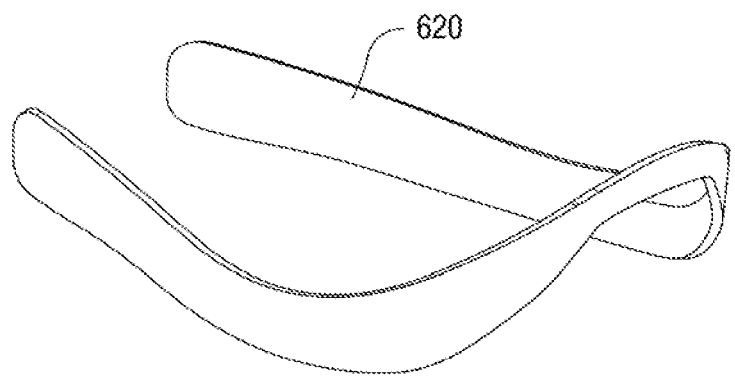
FIGS. 57-66 illustrate a cushion of a patient interface including a reinforcing member constructed according to another embodiment of the present invention.
Figure 58:
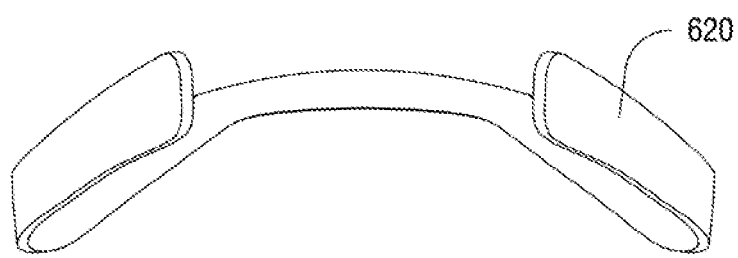
Figure 59:
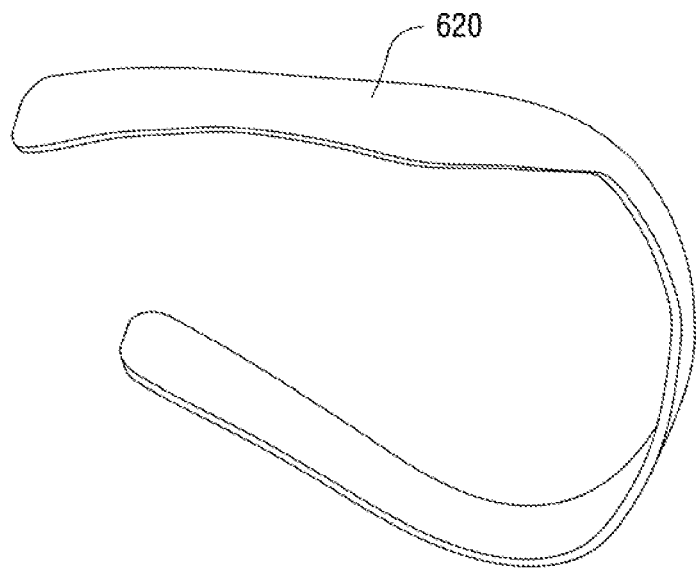
Figure 60:
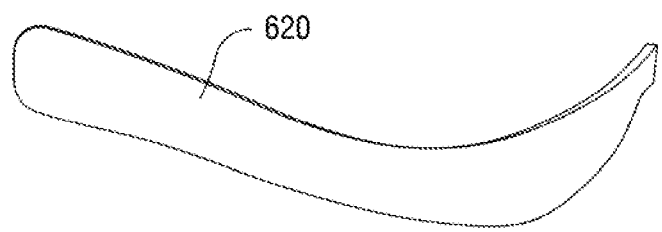
Figure 61:
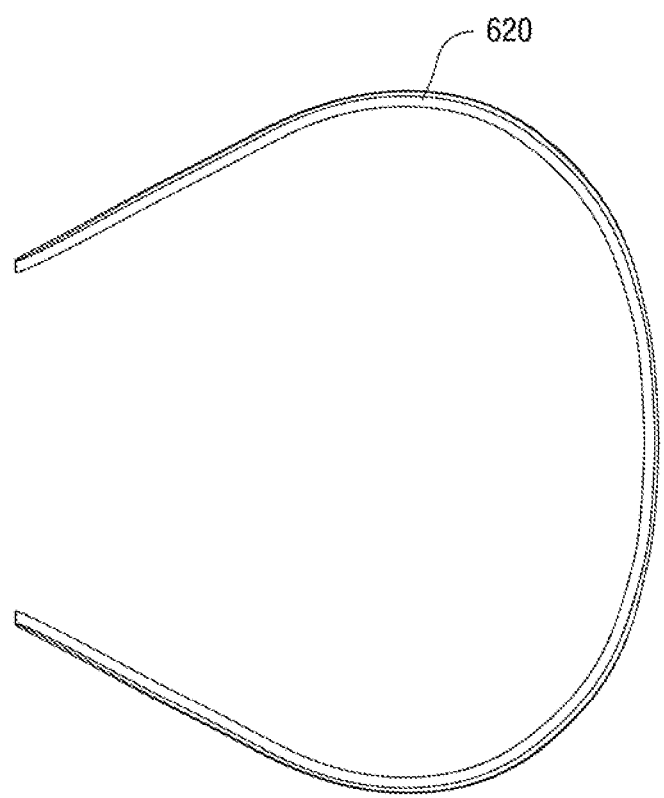
Figure 62:
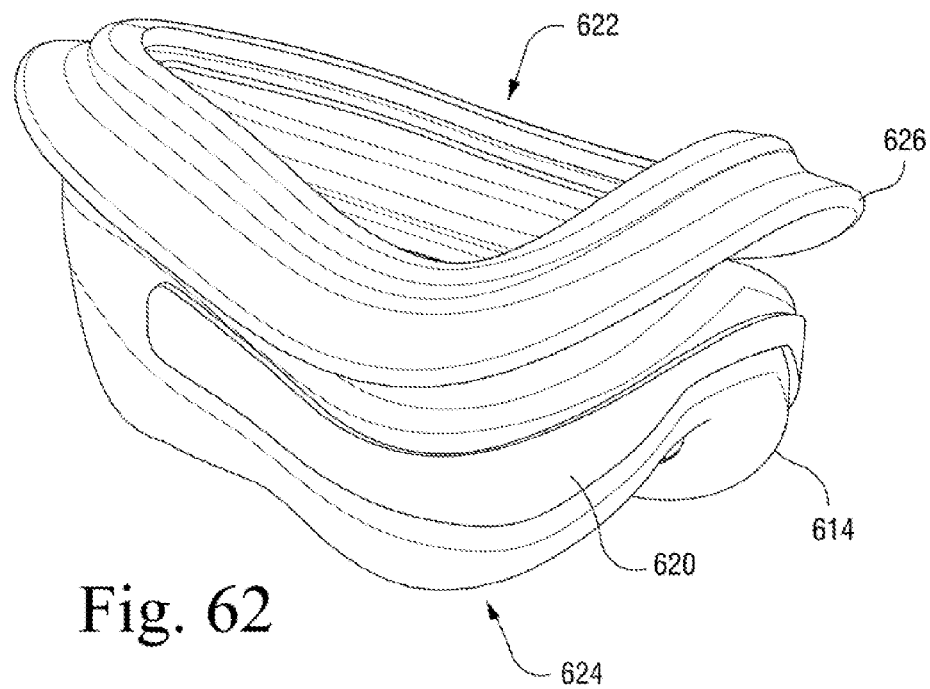
Figure 63:
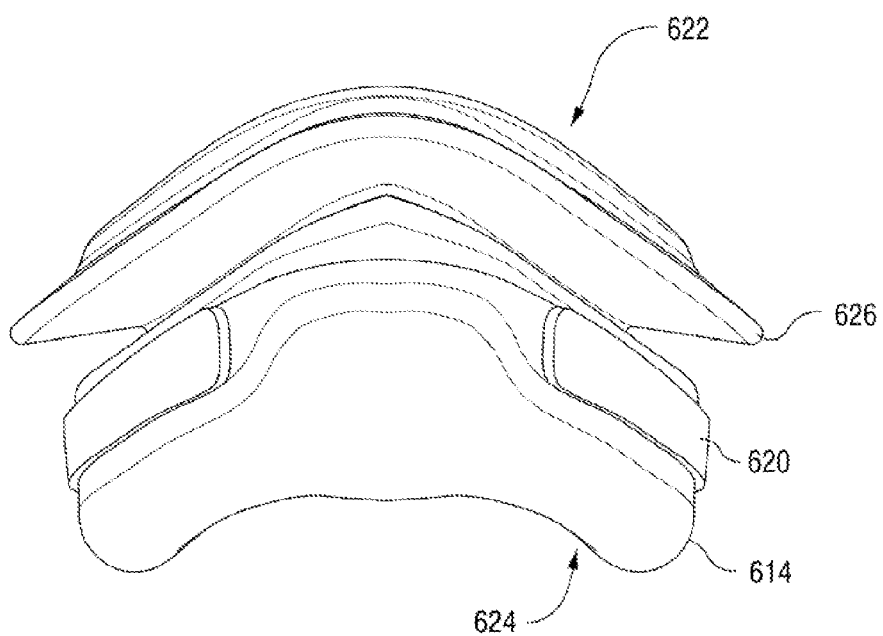
Figure 64:
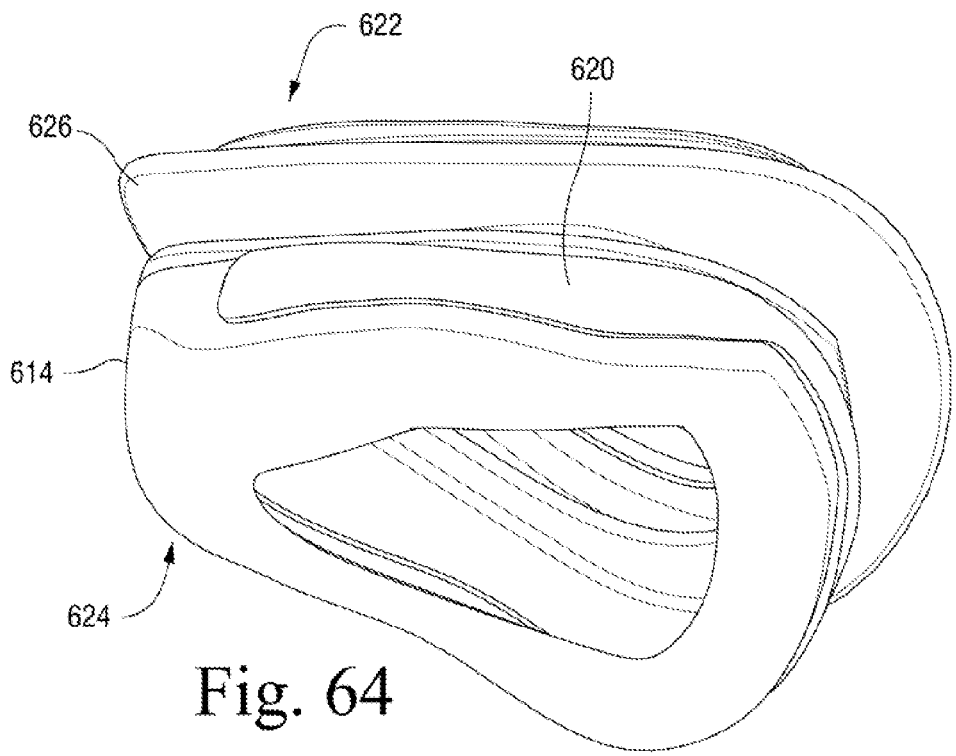
Figure 65:
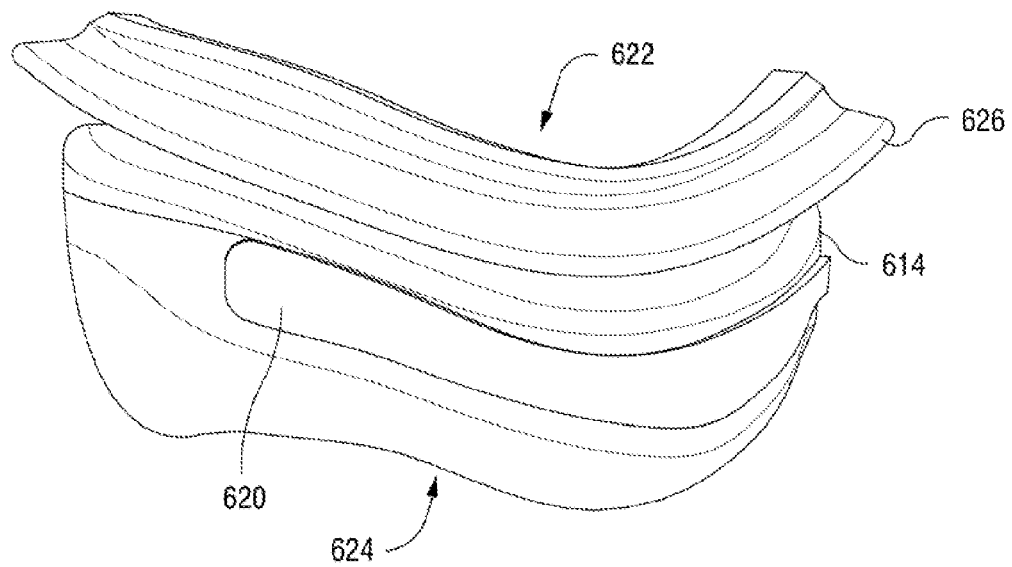
Figure 66:
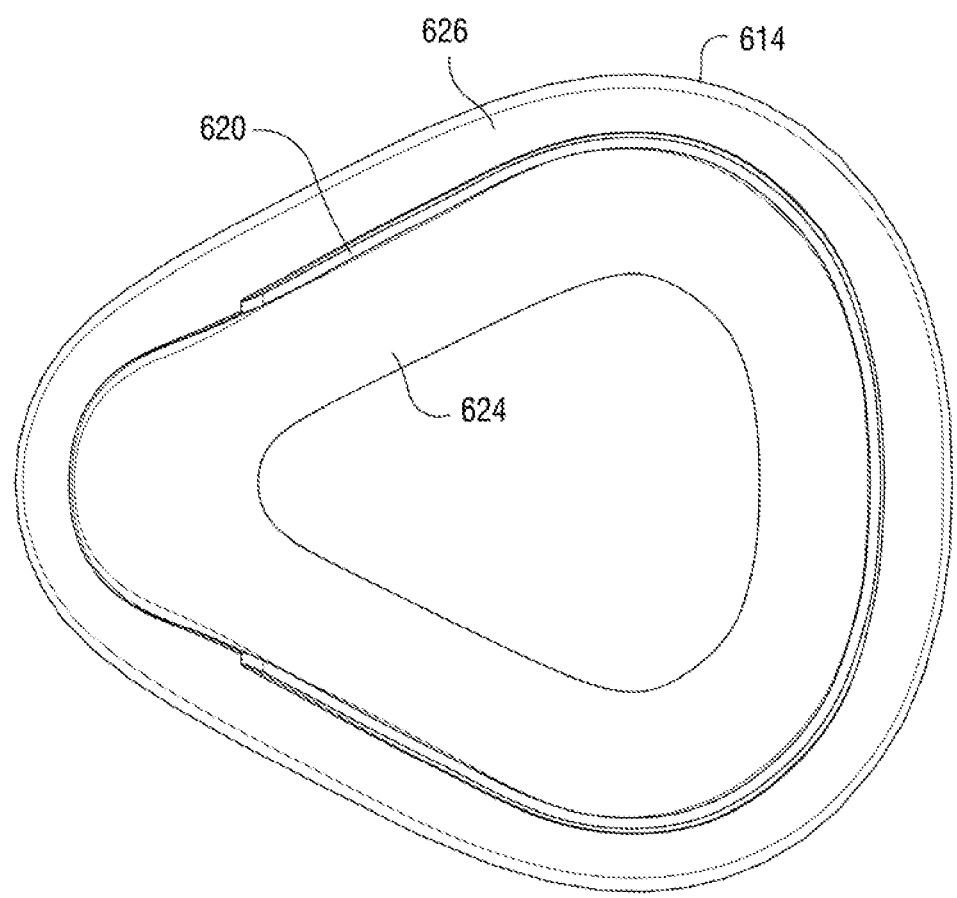
Figure 67:
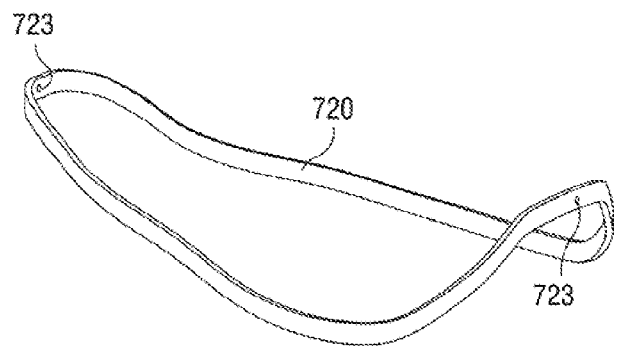
FIGS. 67-76 illustrate a cushion of a patient interface including a reinforcing member constructed according to yet another embodiment of the present invention.
Figure 68:
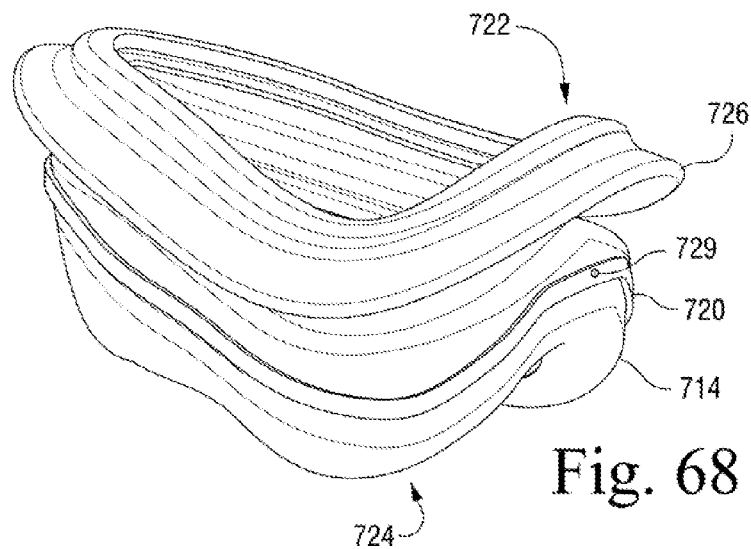
Figure 69:
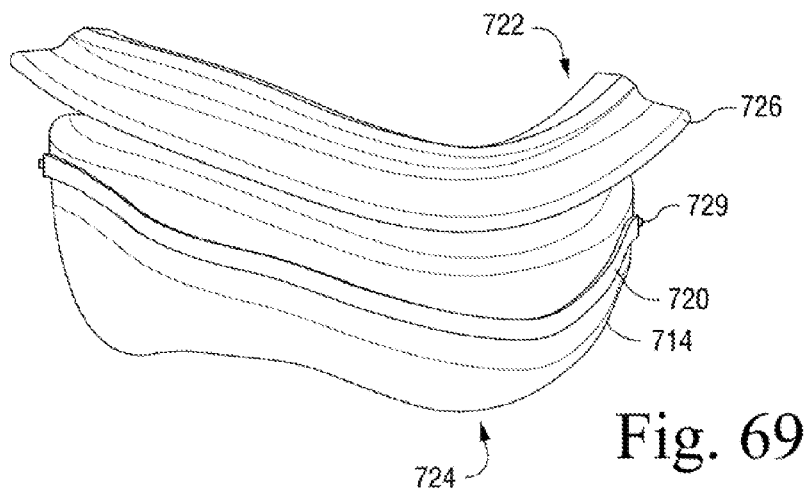
Figure 70:
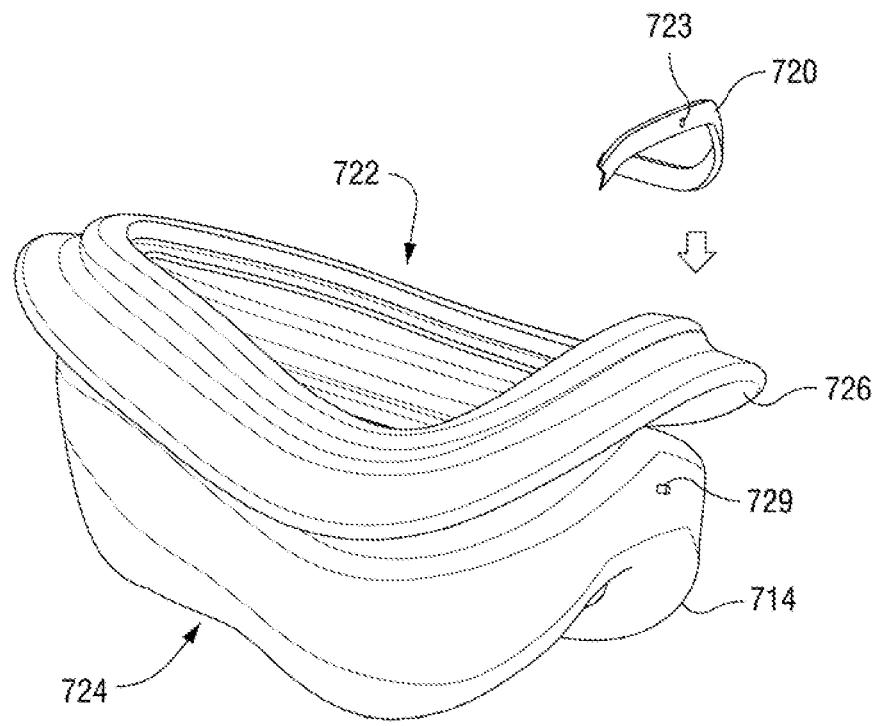
Figure 71:
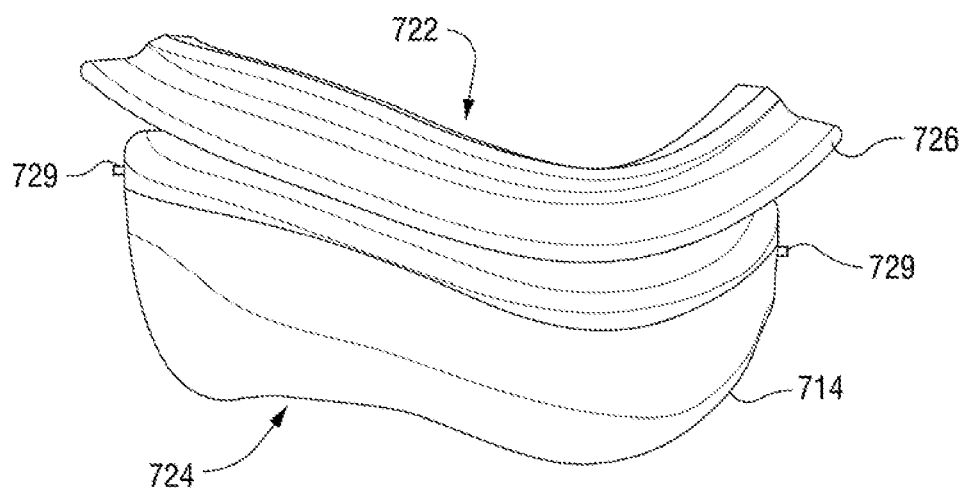
Figure 72:
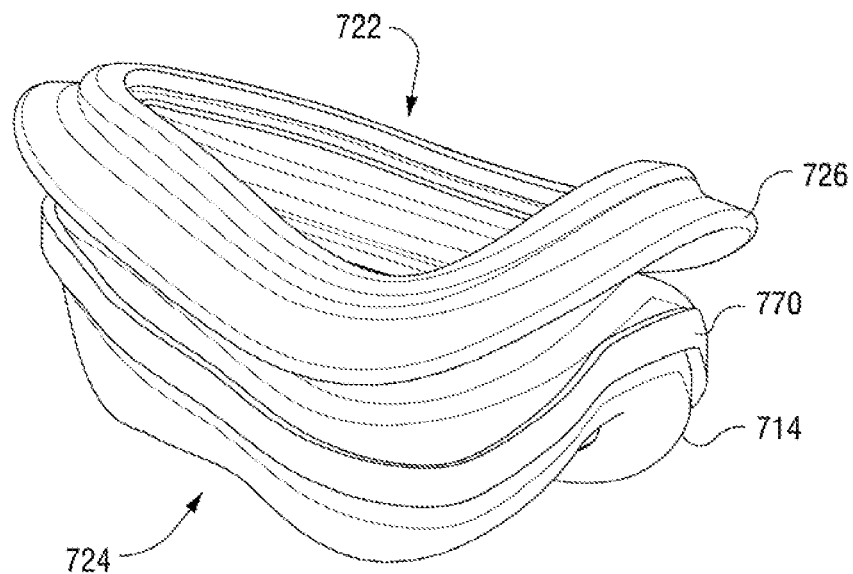
Figure 73:
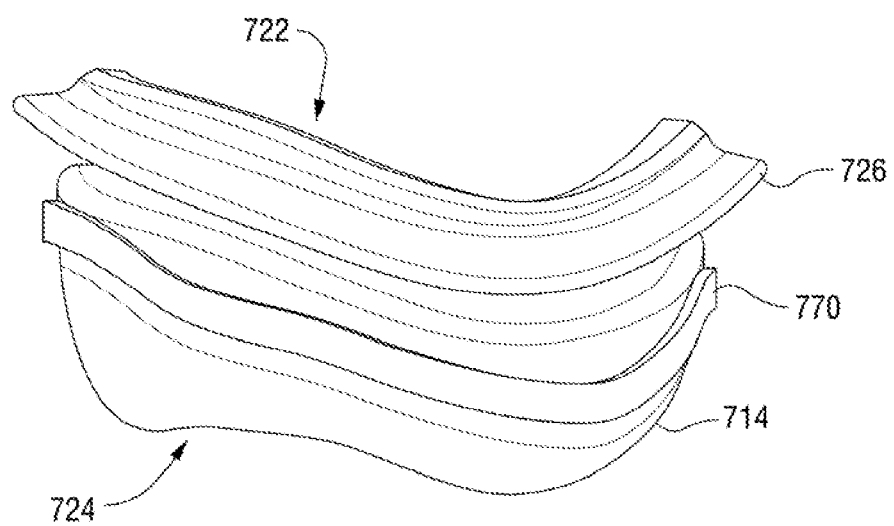

In the illustrated embodiment, the reinforcing member 420 is in the form of a thickened reinforcing section or rib (e.g., a thickened bead of silicone) that is integrally molded with the side wall 428 of the cushion 414. As illustrated, the cushion 414 includes one rib 420 that extends horizontally around the cushion perimeter. However, multiple horizontal ribs 420 are possible. For example, FIG. 50 illustrates a cushion 414 including three horizontal ribs 420.

FIGS. 51-56 illustrate another embodiment of a reinforcing member 520 provided to a cushion 514. As illustrated, the cushion 514 includes a non-face-contacting portion 522, a face-contacting portion 524, and a gusset portion 526 that interconnects the non-face contacting portion 522 and the face-contacting portion 524. The face-contacting portion 524 of the cushion 514 includes a side wall 528, an underlying cushion 530, and a membrane 532 (see FIG. 56).

In the illustrated embodiment, the reinforcing member 520 is in the form of multiple thickened reinforcing sections or ribs 560 (e.g., thickened beads of silicone) that are integrally molded with the side wall 528 of the cushion 514. As illustrated, each rib 560 extends vertically. The ribs 560 are spaced apart from one another and extend around the cushion perimeter to define the reinforcing member 520.

As shown in FIGS. 48-56, the horizontal and vertical ribs 420, 560 are provided on an external surface of the cushion. However, the ribs 420, 560 may be provided on an internal surface of the cushion.

FIGS. 57-66 illustrate another embodiment of a reinforcing member 620 (also referred to as a cushion overclip or saddle overclip) provided to a cushion 614. As shown in FIGS. 62-66, the cushion 614 includes a non-face-contacting portion 622, a face-contacting portion 624, and a gusset portion 626 that interconnects the non-face contacting portion 622 and the face-contacting portion 624.

In the illustrated embodiment, the reinforcing member 620 is in the form of a partial cushion overclip that provides reinforcement to selected regions of the cushion 614. Specifically, the reinforcing member 620 is generally U-shaped and includes a cut-out at a nasal bridge area so that the reinforcing member 620 does not provide support in a nasal bridge area of the cushion 614 in use (depending on gusset type). This arrangement also prevents possible interference of the reinforcing member 620 with the patient's nose in use.

In its operative position, the reinforcing member 620 engages the cushion 614 along a portion of the side wall between the face-contacting portion 624 and the gusset portion 626, e.g., see FIGS. 62-66. The reinforcing member 620 may be glued, mechanically fastened, or overmolded in position.

The reinforcing member 620 is not limited to the design shown in FIGS. 57-66. For example, the reinforcing member 620 may include two or more separate pieces, and the cut-out area provided by the reinforcing member 620 may be located in other areas.

Also, in the illustrated embodiment, the reinforcing member 620 is provided to a portion of an external surface of the side wall of the cushion 614, e.g., to prevent the cushion from over-inflating or billowing out. However, the reinforcing member 620 may be provided to an internal surface of the cushion.

FIGS. 67-76 illustrate another embodiment of a reinforcing member 720 (also referred to as a cushion overclip or saddle overclip) provided to a cushion 714. The cushion 714 includes a non-face-contacting portion 722, a face-contacting portion 724, and a gusset portion 726 that interconnects the non-face contacting portion 722 and the face-contacting portion 724.

In the illustrated embodiment, the reinforcing member 720 is encapsulated in silicone to secure it onto the cushion 714. Specifically, the reinforcing member 720 is first molded separately from the cushion 714 from a substantially rigid plastic material (see FIG. 67). Then, the reinforcing member 720 is mechanically engaged with the cushion 714, i.e., not chemically bonded.

In one embodiment, the rigid plastic cushion overclip 720 is inserted into a tool, and the flexible silicone cushion 714 is molded over the overclip 720, i.e., insert molding.

In another embodiment, the flexible silicone cushion 714 is molded separately from the overclip 720, and the overclip 720 is manually assembled onto the cushion 714. For example, as shown in FIGS. 68-71, the side wall of the cushion 714 includes bosses 729 integrally molded therewith. In the illustrated embodiment, the bosses 729 are provided at two positions, e.g., opposing ends of the cushion 714. However, multiple positions are possible. The bosses 729 assist with locating the overclip 720 in position. Specifically, the overclip 720 includes openings 723, e.g., two openings, that receive respective bosses 729 therethrough.

After the overclip 720 is mechanically engaged with the cushion 714 to provide an overclip/cushion subassembly, a second layer of silicone 770 is locally molded over the overclip/cushion subassembly to encapsulate or encase the overclip 720 (see FIGS. 72-76). That is, the second layer of silicone 770 bonds to the cushion 714 (also referred to as a first layer of silicone), but does not bond to the overclip 720. This results in the overclip 720 being totally encapsulated or encased in silicone, therefore no openings are provided through which dirt or other debris can enter into the cavity where the overclip 720 is located.

Figure 74:
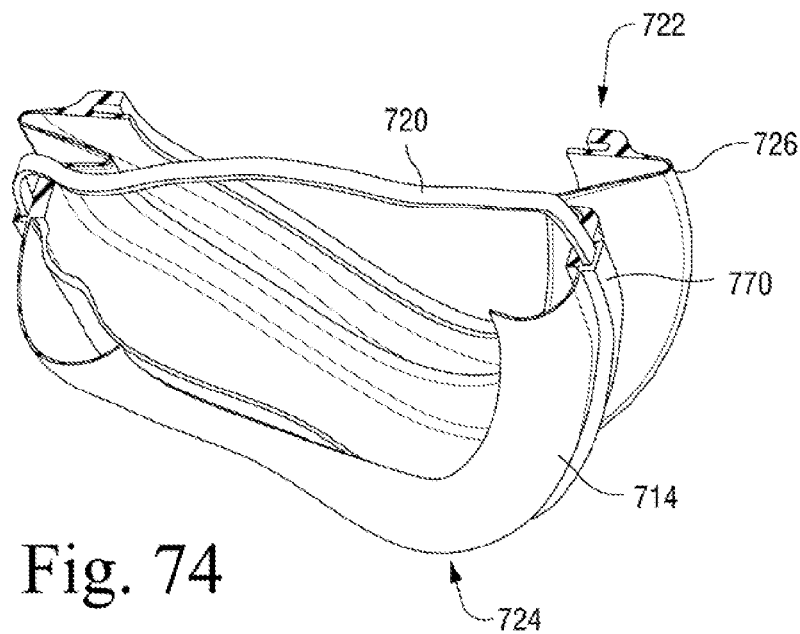
Figure 75:
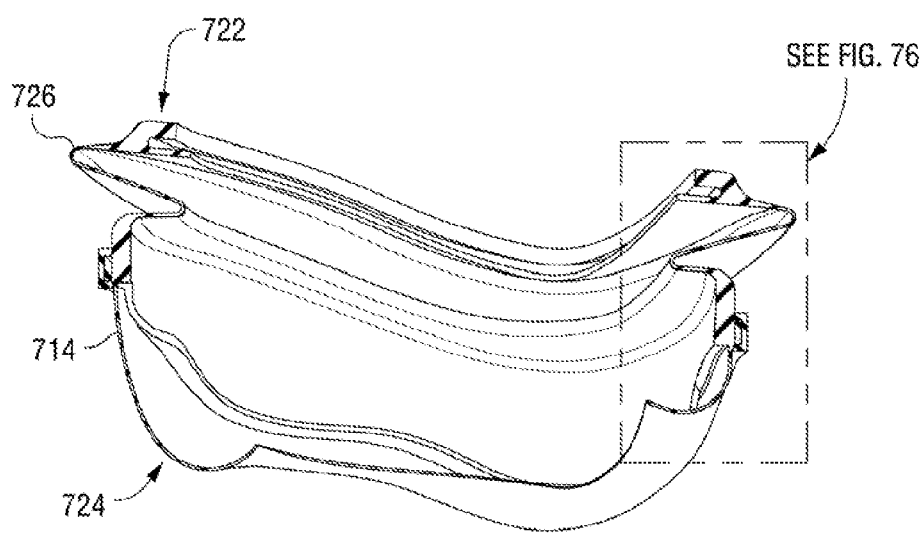
Figure 76:
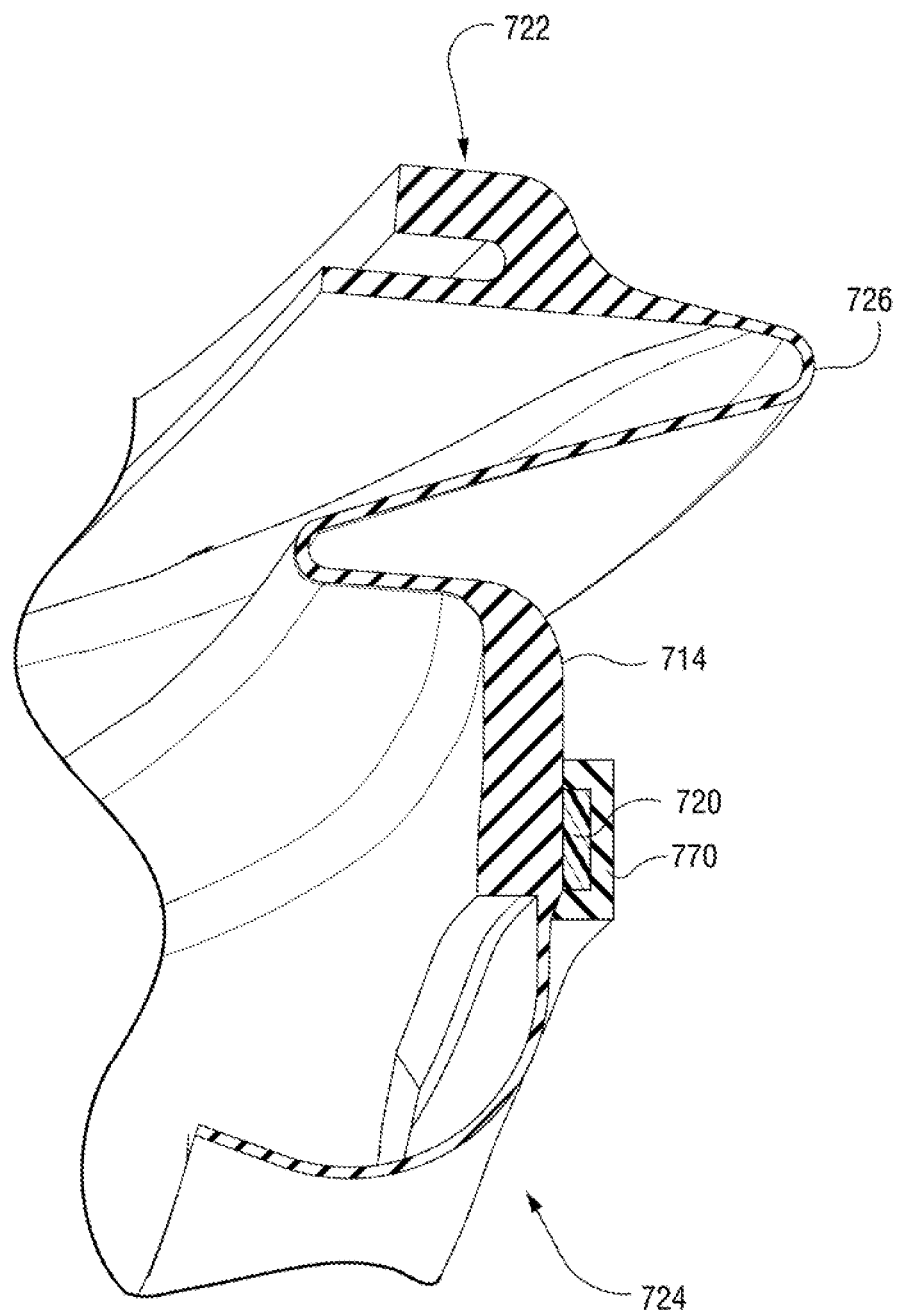
Figure 77:
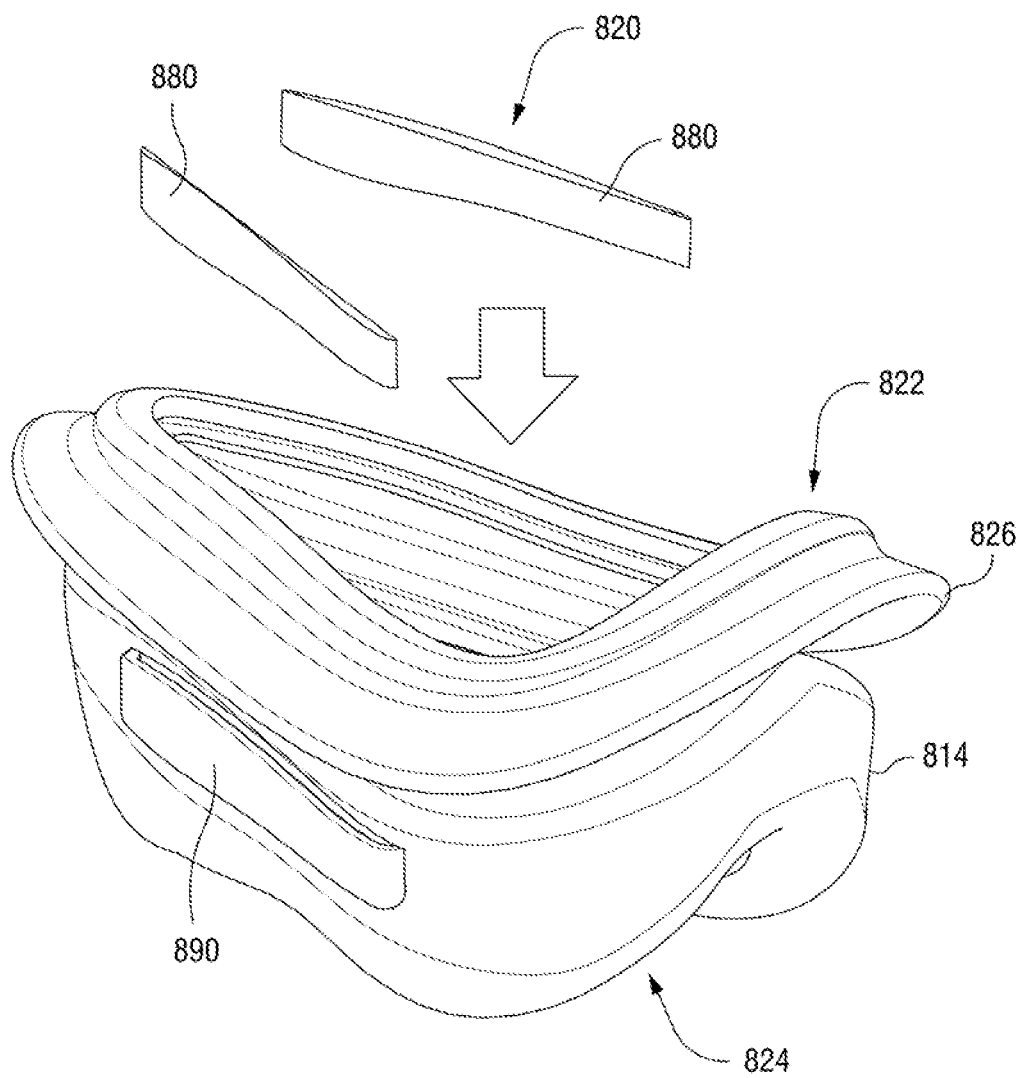
FIGS. 77-82 illustrate a cushion of a patient interface including a reinforcing member constructed according to still another embodiment of the present invention.
Figure 78:
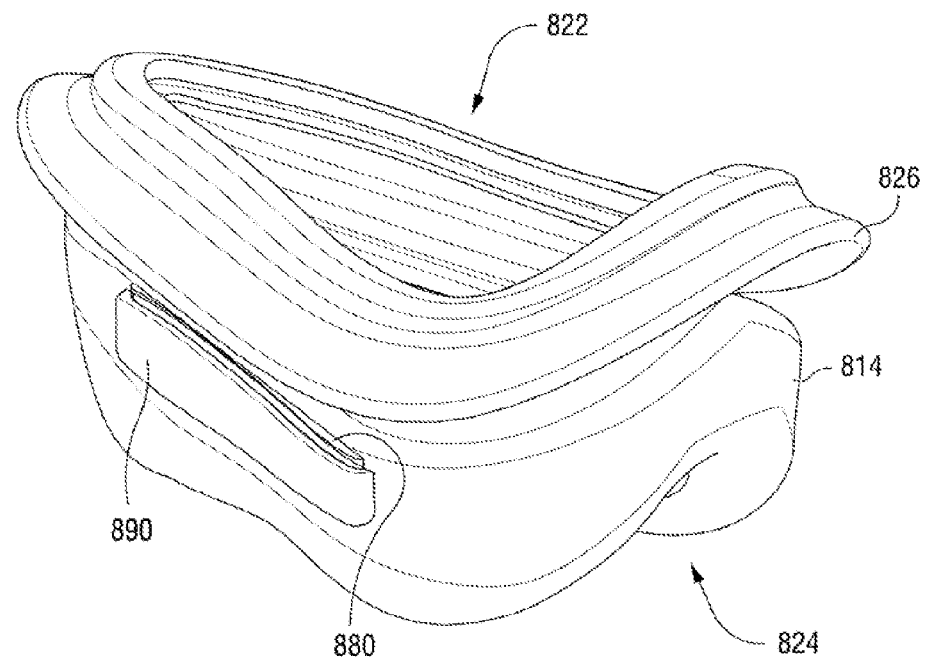
Figure 79:
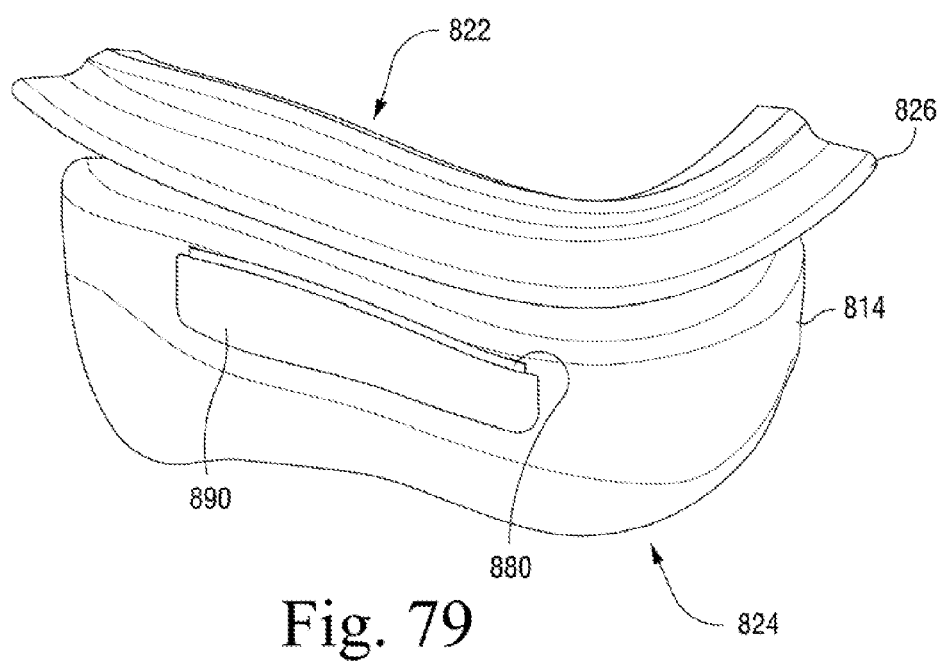
Figure 80:
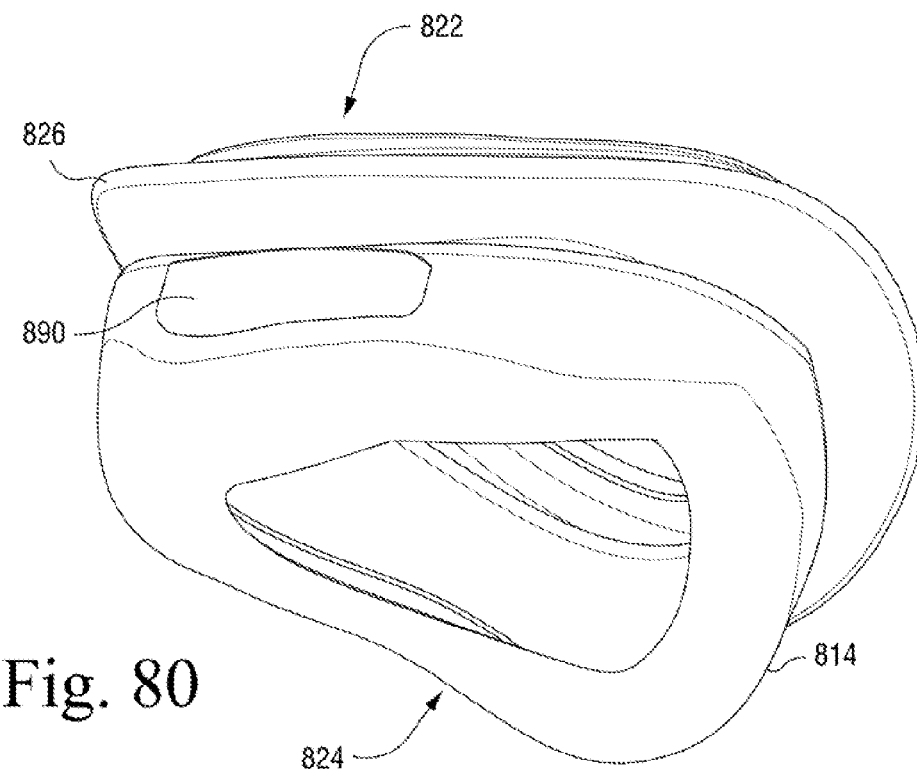
Figure 81:
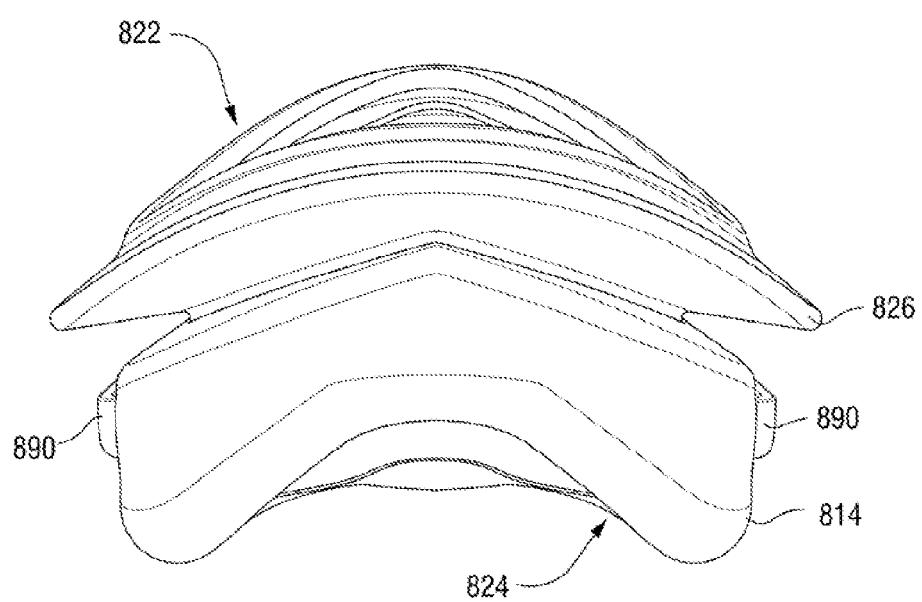

In its operative position, the reinforcing member 720 is supported on the cushion 714 along a portion of the side wall between the face-contacting portion 724 and the gusset portion 726, e.g., see FIGS. 74-76.

FIGS. 77-82 illustrate another embodiment of a reinforcing member 820 provided to a cushion 814. The cushion 814 includes a non-face-contacting portion 822, a face-contacting portion 824, and a gusset portion 826 that interconnects the non-face contacting portion 822 and the face-contacting portion 824.

In the illustrated embodiment, the reinforcing member 820 is in the form of removable rigid plastic inserts 880 that provide reinforcement to selected regions of the cushion 814. Specifically, the reinforcing member 820 includes two inserts 880 that are removably received within respective pockets 890 integrally molded with the cushion 814. However, more than two positions are possible.

In its operative position, the inserts 880 engage the cushion 814 along a portion of the side wall between the face-contacting portion 824 and the gusset portion 826. The inserts 880 are provided to a portion of an external surface of the side wall of the cushion 814 to act as cushion/gusset stiffening elements to prevent the cushion from over-inflating or billowing out. However, the inserts 880 may be provided to an internal surface of the cushion 814.

Although the illustrated embodiments illustrate a reinforcing member being utilized with a cushion including a gusset portion, it should be understood that the reinforcing member may be adapted for use with a cushion without a gusset portion.

Also, although the illustrated embodiments illustrate a reinforcing member being utilized with a full-face mask, it should be understood that the reinforcing member may be adapted for use with other suitable masks, e.g., nasal masks, etc. Specifically, the reinforcing member is particularly useful with full-face masks because the gusset portion of full-face masks, when compared to nasal masks such as the Activa®, extends further into the breathing cavity (e.g., see FIGS. 10-23). This arrangement may be perceived as more susceptible to blowout, and hence the incorporation of the reinforcing member into the full face mask limits or eliminates this blowout.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. For example, the reinforcing member may be applied to only a selected portion or portions of the cushion, such as the cheek regions. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid, obesity, stroke, bariatric surgery, etc.) can derive benefit from the above teachings. Moreover, the above teachings have applicability with patients and non-patients alike in non-medical applications.

What is claimed is:

1. A patient interface comprising:
    a frame;
    a cushion having a non-face-contacting portion connected to the frame and a face-contacting portion adapted to engage the patient's face in use, the face-contacting portion including a side wall and a flexible membrane extending from the side wall; and
    a reinforcing member provided to at least a portion of an interior surface of the side wall of the cushion, the reinforcing member providing reinforcement to the side wall of the cushion to at least limit lateral expansion of the cushion in use,
    wherein the cushion includes a gusset portion that interconnects the non-face-contacting portion and the face-contacting portion and at least a portion of the gusset portion extends radially inwardly from the side wall into a breathing cavity defined by the cushion.

2. The patient interface according to claim 1, wherein the reinforcing member has a width and/or depth that is selectively varied along its length to vary the stiffness and hence a level of reinforcement being provided to selected regions of the cushion.

3. The patient interface according to claim 1, wherein the cushion is structured to sealingly engage around the patient's nose and mouth.

4. The patient interface according to claim 1, wherein the reinforcing member is attached to the cushion such that it is positioned between face-contacting portion and the gusset portion.

5. The patient interface according to claim 1, wherein the gusset portion has a width that varies along the perimeter of the cushion, and the width of the gusset portion and/or side wall along its perimeter is at least partially determinative of the stiffness of the reinforcing member along its length.

6. The patient interface according to claim 1, wherein the face-contacting portion includes an underlying cushion extending from the side wall, and the membrane substantially surrounds the underlying cushion.

7. The patient interface according to claim 1, wherein the reinforcing member has a ring-like structure.

8. The patient interface according to claim 1, wherein the reinforcing member has a shape that corresponds with the shape of the face-contacting portion.

9. The patient interface according to claim 1, wherein the reinforcing member has a generally triangular shape.

10. The patient interface according to claim 1, wherein the cushion includes a channel adapted to receive the reinforcing member therein.

11. The patient interface according to claim 1, wherein the reinforcing member is attached to the cushion by at least one of mechanical fasteners, adhesive, and interference fit.

12. The patient interface according to claim 1, wherein the stiffness of the reinforcing member in cheek regions is greater than the stiffness of the reinforcing member in lower lip and nasal bridge regions.

13. The patient interface according to claim 1, wherein the reinforcing member extends around the entire perimeter of the cushion.

14. The patient interface according to claim 1, wherein the reinforcing member provides support and/or uniformity to the cushion as the cushion moves along a z-axis that extends into the plane of the patient's face.

15. The patient interface according to claim 1, wherein the reinforcing member is assembled to the cushion over the non-face-contacting portion.

16. The patient interface according to claim 1, wherein the reinforcing member includes a flange to assist with positioning and retention.

17. The patient interface according to claim 1, wherein the reinforcing member is provided only to one or more selected portions of the cushion.

18. The patient interface according to claim 1, wherein the cushion includes integrally molded tabs that extend through respective openings provided in the reinforcing member to secure the reinforcing member in position.

19. The patient interface according to claim 1, wherein at least a portion of the gusset portion includes a pair of radially inwardly extending gussets that extend radially inwardly into the breathing cavity defined by the cushion.

20. A patient interface comprising:
    a frame;
    a cushion having a non-face-contacting portion connected to the frame, a face-contacting portion adapted to engage the patient's face in use, and a guest portion that interconnects the non-face-contacting portion and the face-contacting portion; and
    a reinforcing member including multiple thickened reinforcing sections or ribs provided to the cushion between the face-contacting portion and the gusset portion,
    wherein the thickened reinforcing sections or ribs include different lengths in different regions along a perimeter of the cushion that correspond to variation of the gusset portion along the perimeter of the cushion.

* * * * *